US008841098B2

(12) United States Patent
Payne et al.

(10) Patent No.: US 8,841,098 B2
(45) Date of Patent: Sep. 23, 2014

(54) ENZYMES USEFUL FOR PERACID PRODUCTION

(71) Applicant: E. I. du Pont de Nemours and Company, Wilmington, DE (US)

(72) Inventors: Mark Scott Payne, Wilmington, DE (US); Robert DiCosimo, Chadds Ford, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/799,812

(22) Filed: Mar. 13, 2013

(65) Prior Publication Data

US 2013/0288316 A1    Oct. 31, 2013

Related U.S. Application Data

(60) Provisional application No. 61/618,390, filed on Mar. 30, 2012.

(51) Int. Cl.
| | | |
|---|---|---|
| *C12P 7/40* | (2006.01) | |
| *C12N 9/96* | (2006.01) | |
| *C12N 9/18* | (2006.01) | |
| *A61L 9/00* | (2006.01) | |
| *C11D 3/386* | (2006.01) | |

(52) U.S. Cl.
CPC ... *C12N 9/18* (2013.01); *C12P 7/40* (2013.01); *C11D 3/38636* (2013.01)
USPC .......... 435/135; 435/136; 435/197; 424/78.1; 424/94.6

(58) Field of Classification Search
CPC .......... C12P 7/40; C11D 3/38636; C12N 9/20
See application file for complete search history.

(56) References Cited

U.S. PATENT DOCUMENTS

| | | | |
|---|---|---|---|
| 3,974,082 | A | 8/1976 | Weyn |
| 4,585,150 | A | 4/1986 | Beacham et al. |
| 5,116,575 | A | 5/1992 | Badertscher et al. |
| 5,296,161 | A | 3/1994 | Wiersema et al. |
| 5,338,676 | A | 8/1994 | Mitsushima et al. |
| 5,364,554 | A | 11/1994 | Stanislowski et al. |
| 5,398,846 | A | 3/1995 | Corba et al. |
| 5,528,152 | A | 6/1996 | Hinoshita et al. |
| 5,552,018 | A | 9/1996 | Devenyns |
| 5,624,634 | A | 4/1997 | Brougham et al. |
| 5,683,724 | A | 11/1997 | Hei et al. |
| 5,932,532 | A | 8/1999 | Ghosh et al. |
| 6,183,807 | B1 | 2/2001 | Gutzmann et al. |
| 6,210,639 | B1 | 4/2001 | Vlass et al. |
| 6,319,888 | B2 | 11/2001 | Wei et al. |
| 6,391,840 | B1 | 5/2002 | Thompson et al. |
| 6,518,307 | B2 | 2/2003 | McKenzie et al. |
| 6,545,047 | B2 | 4/2003 | Gutzmann et al. |
| 6,995,125 | B2 | 2/2006 | Dasque et al. |
| 7,550,420 | B2 | 6/2009 | DiCosimo et al. |
| 7,723,083 | B2 | 5/2010 | DiCosimo et al. |
| 7,910,347 | B1 | 3/2011 | DiCosimo et al. |
| 7,923,233 | B1 | 4/2011 | DiCosimo et al. |
| 7,927,854 | B1 | 4/2011 | DiCosimo et al. |
| 7,932,072 | B1 | 4/2011 | DiCosimo et al. |
| 7,951,566 | B2 | 5/2011 | DiCosimo et al. |
| 7,960,528 | B1 | 6/2011 | DiCosimo et al. |
| 7,964,378 | B2 | 6/2011 | DiCosimo et al. |
| 8,062,875 | B2 | 11/2011 | DiCosimo et al. |
| 8,206,964 | B2 | 6/2012 | DiCosimo et al. |
| 8,389,254 | B2 | 3/2013 | DiCosimo et al. |
| 8,389,255 | B2 | 3/2013 | DiCosimo et al. |
| 2003/0026846 | A1 | 2/2003 | Hei et al. |
| 2005/0008526 | A1 | 1/2005 | Bianchetti et al. |
| 2005/0139608 | A1 | 6/2005 | Muehlhausen et al. |
| 2008/0176299 | A1 | 7/2008 | DiCosimo et al. |
| 2010/0086510 | A1 | 4/2010 | DiCosimo et al. |
| 2010/0086621 | A1 | 4/2010 | DiCosimo et al. |
| 2011/0236336 | A1 | 9/2011 | DiCosimo et al. |
| 2011/0236338 | A1 | 9/2011 | DiCosimo et al. |
| 2012/0317733 | A1 | 12/2012 | Chisholm et al. |
| 2012/0328534 | A1 | 12/2012 | Butterick et al. |

FOREIGN PATENT DOCUMENTS

| | | |
|---|---|---|
| EP | 1040222 B1 | 10/2000 |
| EP | 0807156 B1 | 3/2001 |
| WO | WO 00/61713 A1 | 3/2000 |
| WO | WO 2011/119706 A1 | 9/2011 |

OTHER PUBLICATIONS

Cantarel et al., The Carbohydrate-Active EnZymes database (CAZy): an expert resource for Glycogenomics, *NAR* 37:D233-D238 (2009).
Mitsushima et al Gene Cloning, Nucleotide Sequence, and Expression . . . , Appl. Env. Microbiol. 61(6):2224-2229, 1995.
Vincent et al., Multifunctional Xylooligosaccharide/Cephalosporin C Deacetylase . . . , J. Mol. Biol., 330:593-606, 2003.
National Center for Biotechnology Information, Nelson et al., Acetyl Xylan Esterase [*Thermotoga maritima* MSB8], Accession No. NP 227893.1, submitted Jun. 1, 1999.
National Center for Biotechnology Information, Land et al,, Acetyl Xylan Esterase [*Actinosynnema mirum* DSM 43827], Accession No. ACU35776.1, submitted May 29, 2009.

(Continued)

*Primary Examiner* — Tekchand Saidha
*Assistant Examiner* — Md. Younus Meah

(57) ABSTRACT

Acetyl xylan esterases and variants thereof having perhydrolytic activity are provided for producing peroxycarboxylic acids from carboxylic acid esters and a source of peroxygen. Multi-component peracid generation systems comprising an enzyme catalyst having perhydrolytic activity are also provided, as are methods of using the present enzyme catalyst to produce peroxycarboxylic acids. The polypeptide having perhydrolytic activity may be used to produce peroxycarboxylic acids suitable for use in a variety of applications such as cleaning, disinfecting, sanitizing, bleaching, wood pulp processing, paper pulp processing, and personal care applications.

16 Claims, 2 Drawing Sheets

(56) References Cited

OTHER PUBLICATIONS

National Center for Biotechnology Information, Brzuszkiewicz et al., Putative Acetyl Xylan Esterase [*Propionibacterium acnes* 266], Accession No. AEE71478.1, submitted Nov. 17, 2010.

National Center for Biotechnology Information, Holden et al., Putative Acetyl Xylan Esterase (AXE1) Family Protein [*Streptococcus equi* subsp. zooepidemicus], Accession No. CAX00506.1, submitted Aug. 8, 2008.

National Center for Biotechnology Information, Munk et al., Acetyl xylan esterase [*Stackebrandtia nassauensis* DSM 44728], Accession No. ADD42786.1, submitted Oct. 1, 2009.

National Center for Biotechnology Information, Tettelin et al., acetyl xylan esterase, putative [*Streptococcus agalactiae* 2603V/R], Accession No. AAM98949,1, submitted Jul. 18, 2002.

National Center for Biotechnology Information, Land et al., Acetyl xylan esterase [*Actinosynnema mirum* DSM 43827], Accession No. ACU35776.1, submitted May 29, 2009.

Co-pending U.S. Appl. No. 13/799,757, filed Mar. 13, 2013.
Co-pending U.S. Appl. No. 13/799,882, filed Mar. 13, 2013.
Co-pending U.S. Appl. No. 13/799,930, filed Mar. 13, 2013.
Co-pending U.S. Appl. No. 13/800,016, filed Mar. 13, 2013.

Database UniProt (Online) SubName: Full=Putative Acetyl xylan esterase; version 12, XP002698284, retrieved from EBI accession No. UNIPROT: D3QAK3, Database accession No. D3QAK3, Feb. 22, 2012.

International Search Report and Written Opinion of the International Searching Authority in PCT/US2013/030760, issued Jun. 24, 2013.

SEQ ID NO: 2    MAFFDLPLEELKKYRPERYEEKDFDEFWEETLAESEKFPLDPVFERMES-HLKTVEAYDV
SEQ ID NO: 4    MPWFDLPEAELAQYRTPTPEPAGLDAWWAERLAEARALAEPVTSTPHEESAYGPLGVRDV
SEQ ID NO: 6    MPLTDLGIDEARTYRPNVPEPDGFDSFWAETLDEYSGVPQDLTAVPFDN-RQALIDTWDL
SEQ ID NO: 8    -MIETMSLEEMMSYRGRHEVPKDFDHFWETCIKENQ-AASYQLDQKDFG--LDFADCYEL
SEQ ID NO:10    MPLFDFPLDELRAYRPEPDEPQDFDAFWDRTSEVADRHPLDVRLTPQPG-HLGLVDVWDV
SEQ ID NO:12    -MIETMSLDDMREYLGQDQIPEDFDDFWKKQTMKYQGNIEYRLDKKDFN--ITFAQAYDL
                  :        :    .     :    *   :*   .    . :     .    : :

SEQ ID NO: 2    TFSGYRGQRIKGWLLVPKLEEEKLPCVVQYIGYNGGRGFPHDWLFWPSMGYICFVMDTRG
SEQ ID NO: 4    EFSGALGDRVRAWHLRPAG-DDPLPTAVVFIGYGGGRGTPTEHAWLAAAGYGVLVVDTRG
SEQ ID NO: 6    SWAGYHNSRVSGWLHAPAAVNGPLPLVIEYLGYSSSRGVPIG-SVFAAAGYAHIVVDPRG
SEQ ID NO: 8    RFKGSNGSTIYAKCVFPKA-KQLVPVVFYFHGYQOGQSPDWSDQFNYLAAGYAVVSMDVRG
SEQ ID NO:10    RFAGWNGDPINAWLIAPAG-ASRVGCVVTYIGYHGGRGFPHQHLRWPVAGWATLVVDTRG
SEQ ID NO:12    HFKGSNNSIVYAKCLFPKT-NKPYPVVFYFHGYQNQSPDWSDQLNYVAAGYGVVSMDVRG
                  .  .   .      *       .. ::: **  .   .        . :  .* **

SEQ ID NO: 2    QG--SGWLKGDTPDYPEGPVDPQYPGFMTRGILD-PRTYYYRRVFTDAVRAVEAAAASFPQ
SEQ ID NO: 4    QGG-RWTTGATADSAPSG---PSHPGFMTRGITS-PEGYYYTRLMTDAALAVDVAAGLDG
SEQ ID NO: 6    QGWGHPTLTENCPDVHDG---SGAPGFMTQSLSD-PHGHYYRRLFTDAFRCLQAAREMEL
SEQ ID NO: 8    QAG-----YSQDLGQFDG---ITVKGQVIRGMTSGPEQLFYKDVYLDVYQLIDIVSAFAR
SEQ ID NO:10    QGA-SASASSGVTGDPHGSEFGHAPGMLTKGILD-PDEYYYRRVFTDAARAVDVAASLDI
SEQ ID NO:12    QAG-----QSQDKGHFDG---ITVKGQIVRGMISGPNHLFYKDIYLDVFQLIDIIATLES
                *.          .   .            .     . :   *  *    :     :

FIG.1A

```
SEQ ID NO:2    VDQERIVIAGGSQGGGIALAVSALSKK----AKALLCDVPFLCHFRRAVQLV-DTHPYAE
SEQ ID NO:4    VDPERIAVLGASQGGGLALAAAALNPT---KVKVCHADVPFLCDFQRAITLT-GADPYAE
SEQ ID NO:6    VDPTRIAVLGHSQGGGQAIAVCALAAMRGIKLAGAFVDVPFLCHIRRSCDIA-TDGPYLE
SEQ ID NO:8    VDDSRLYSYGWSQGGGALSLIAAALHPK--IAKTVAVYPFLSDFKRVLELGNHSEPYDE
SEQ ID NO:10   VDESRIVVSGHSQGGGIAQAVSALRPG----VAAALVNEPFLCHFRRSCEIA-STGPYPE
SEQ ID NO:12   VDSNQLYSYGWSQGGGALALIAAALNPK----IVKTVAVYPFLSDFRRVLDLGGVSEPYDE
               ** :: **** . . ** ***..::*. : **

SEQ ID NO:2    ITNFLKTHR---DKEEIVFRTLSYFDGVNFAARAKIPALFSVGLMDNICPPSTVFAAYNY
SEQ ID NO:4    IANFLSHNV---ALVKQVRETLTYVDAALLSRRITATSLLSAGLMDEVCPPSTVFAAYNE
SEQ ID NO:6    VVRYLAAHP---SLCGRAFQTLGYFDGLHFARRARTSTWFSVAMMDQAVPPSSVWAAYNA
SEQ ID NO:8    LFRYFKYHDPFHDTEAEVLGNLAYIDVKNFAHLITCPVVMLTCMEDVICPPSTQFAIFNR
SEQ ID NO:10   LVAFLGAQR---DLEQRVFATLSYFEGMSFASRAQAPALYSVALMDTTCPPSTVFAAYNR
SEQ ID NO:12   LFRYFKYSDPFHKTENNVLKTLAYIDVKNFAHRISCPVVLLTALKDDICPPSTQFAIFNR
               : :: * . * . : : *

SEQ ID NO:2    YAG-----PKEIRIYPYNNHEGGSFQAVEQVKFLKKLFEKG------
SEQ ID NO:4    ITA-----PKRIEVFPFSGHAVPR-THDEVKLKHLREHL--------
SEQ ID NO:6    WGDGMVADKHIAVYPFAGHAAGEDVQRWNQLGVLAQLFS--------
SEQ ID NO:8    LAT---ADKCHKLIPDYGHDPMGVKVKDFIFDQLTGSHFTKA-----
SEQ ID NO:10   WAG---PKDIEVWPWNGHSGGEGYHAQRQLEWLSERFGTG-------
SEQ ID NO:12   LTS---TKK-HLLLPDYGHDPMTVQVKDHIFDQLTGSQFTKQKIE
               * *. *
```

FIG. 1B

ENZYMES USEFUL FOR PERACID PRODUCTION

CROSS-REFERENCE TO RELATED APPLICATION

This application claims the benefit of U.S. Provisional Application No. 61/618,390 filed Mar. 30, 2012, which is incorporated by reference in its entirety.

TECHNICAL FIELD

This disclosure relates to the field of peroxycarboxylic acid biosynthesis and enzyme catalysis. More specifically, multi-component peracid generation systems comprising an enzyme catalyst having perhydrolytic activity are provided. Methods of using the present enzyme catalyst to produce peroxycarboxylic acids are also provided.

BACKGROUND

Peroxycarboxylic acid compositions can be effective antimicrobial agents. Methods of using peroxycarboxylic acids to clean, disinfect, and/or sanitize hard surfaces, textiles, meat products, living plant tissues, and medical devices against undesirable microbial growth have been described (U.S. Pat. No. 6,545,047; U.S. Pat. No. 6,183,807; U.S. Pat. No. 6,518,307; U.S. Patent Application Publication No. 2003-0026846; and U.S. Pat. No. 5,683,724). Peroxycarboxylic acids have also been used in various bleaching applications including, but not limited to, wood pulp bleaching/delignification and laundry care applications (European Patent 1040222B1; U.S. Pat. No. 5,552,018; U.S. Pat. No. 3,974,082; U.S. Pat. No. 5,296,161; and U.S. Pat. No. 5,364,554). The desired efficacious concentration of peroxycarboxylic acid may vary according to the product application (for example, ca. 500 ppm to 1000 ppm for medical instrument disinfection, ca. 30 ppm to 80 ppm for laundry bleaching or disinfection applications) in 1 min to 5 min reaction time at neutral pH.

Enzymes structurally classified as members of family 7 of the carbohydrate esterases (CE-7) have been employed as perhydrolases to catalyze the reaction of hydrogen peroxide (or alternative peroxide reagent) with alkyl esters of carboxylic acids in water at a basic to acidic pH range (from ca. pH 10 to ca. pH 5) to produce an efficacious concentration of a peroxycarboxylic acid for such applications as disinfection (such as medical instruments, hard surfaces, textiles), bleaching (such as wood pulp or paper pulp processing/delignification, textile bleaching and laundry care applications), and other laundry care applications such as destaining, deodorizing, and sanitization, and personal care applications (U.S. Pat. Nos. 7,964,378; 7,951,566; and 7,723,083; Published U.S. Patent Application No. 2008-0176299 to DiCosimo et al.; and Published U.S. Patent Application Nos. 2012-0317733 and 2012-0328534 to Chisholm et al.). The CE-7 enzymes have been found to have high specific activity for perhydrolysis of esters, particularly acetyl esters of alcohols, diols and glycerols. Variant CE-7 perhydrolases derived from several species having improved performance been reported by DiCosimo et al. (U.S. Pat. Nos. 7,927,854; 7,923,233; 7,932,072; 7,910,347; 7,960,528; 8,062,875; 8,206,964; 8,389,254; and 8,389,255; and Published U.S. Patent Application Nos. 2011-0236336 and 2011-0236338).

Previously reported CE-7 carbohydrate esterases having perhydrolytic activity (both wild type and variants thereof) comprised a conserved structural "signature" motif as defined by Vincent et al. (*J. Mol. Biol.*, 330:593-606 (2003)). More specifically, the CE-7 signature motif used to structurally identify and define members of the CE-7 carbohydrate esterase family comprises three conserved submotifs: 1) an "RGQ" submotif of Arg118-Gly119-Gln120, 2) a "GXSQG" submotif of Gly186-Xaa187-Ser188-Gln189-Gly190, and 3) an "HE" submotif of His303-Glu304 (residue numbering and orientation relative to the *Thermotoga maritima* reference sequence provided as SEQ ID NO: 2).

While the vast majority of enzymes classified as CE-7 carbohydrate esterases are comprised of the signature motif defined by Vincent et al., several polypeptide sequences have been added to family 7 of the carbohydrate esterases that do not contain the "HE" submotif (Cantarel et al., "The Carbohydrate-Active EnZymes database (CAZy): an expert resource for Glycogenomics", *NAR*, 37:D233-D238 (2009)). The presence of perhydrolytic activity within this subgroup has not been reported.

Incorporation of perhydrolytic enzyme technology into some applications may require the identification of new perhydrolytic enzymes. As such, there remains a need to identify additional enzyme catalysts comprising polypeptide having significant perhydrolytic activity.

SUMMARY

Several enzymes have been identified having perhydrolytic activity suitable for the production of peracids at efficacious concentrations.

In one embodiment, an enzymatic peracid generation system is provided comprising a set of reaction components comprising:

(1) at least one substrate selected from the group consisting of:
  (i) one or more esters having the structure $[X]_m R_5$ wherein
  X=an ester group of the formula $R_6$—C(O)O;
  $R_6$=a C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
  $R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester or carboxylic acid group; wherein $R_5$ optionally comprises one or more ether linkages;
  m=an integer ranging from 1 to the number of carbon atoms in $R_5$; and wherein said esters have solubility in water of at least 5 ppm at 25° C.;
  (ii) one or more glycerides having the structure

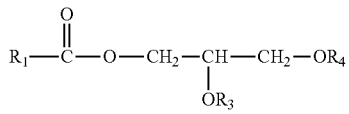

wherein $R_1$=a C1 to C21 straight chain or branched chain alkyl optionally substituted with an hydroxyl or a C1 to C4 alkoxy group and $R_3$ and $R_4$ are individually H or $R_1$C(O);

(iii) one or more esters of the formula:

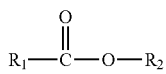

wherein $R_1$=a C1 to C7 straight chain or branched chain alkyl optionally substituted with an hydroxyl or a C1 to C4 alkoxy group and $R_2$=a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10;

(iv) one or more acetylated monosaccharides, acetylated disaccharides, or acetylated polysaccharides; and (v) any combination of (i) through (iv);

(2) a source of peroxygen; and (3) an enzyme catalyst comprising a polypeptide having perhydrolytic activity and an amino acid sequence having at least 80% identity to the amino acid sequence set forth in SEQ ID NO: 10, provided that the amino acid residue bound to the C-terminal side of the catalytic histidine is not glutamic acid;

whereby a peracid is enzymatically produced upon combining the reaction components under suitable reaction conditions.

In another embodiment, a process for producing a peroxycarboxylic acid is also provided comprising:

(a) providing a set of reaction components comprising:
  (1) at least one substrate selected from the group consisting of:
    (i) one or more esters having the structure $[X]_mR_5$ wherein
X=an ester group of the formula $R_6$—C(O)O;
$R_6$=a C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester or carboxylic acid group; wherein $R_5$ optionally comprises one or more ether linkages;
m=an integer ranging from 1 to the number of carbon atoms in $R_5$; and wherein said esters have solubility in water of at least 5 ppm at 25° C.;

(ii) one or more glycerides having the structure

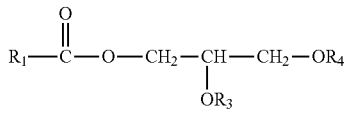

wherein $R_1$=a C1 to C21 straight chain or branched chain alkyl optionally substituted with an hydroxyl or a C1 to C4 alkoxy group and $R_3$ and $R_4$ are individually H or $R_1C(O)$;

(iii) one or more esters of the formula:

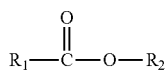

wherein $R_1$=a C1 to C7 straight chain or branched chain alkyl optionally substituted with an hydroxyl or a C1 to C4 alkoxy group and $R_2$=a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10;

(iv) one or more acylated monosaccharides, acylated disaccharides, or acylated polysaccharides; and (v) any combination of (i) through (iv);

(2) a source of peroxygen; and (3) an enzyme catalyst comprising a polypeptide having perhydrolytic activity and an amino acid sequence having at least 80% identity to the amino acid sequence set forth in SEQ ID NO: 10, provided that the amino acid residue bound to the C-terminal side of the catalytic histidine is not glutamic acid;

(b) combining the set of reaction components under suitable reaction conditions whereby peroxycarboxylic acid is produced; and (c) optionally diluting the peroxycarboxylic acid produced in step (b).

In another embodiment, a process is provided further comprising a step (d) wherein the peroxycarboxylic acid produced in step (b) or step (c) is contacted with a hard surface, a body surface, or at least one an article of clothing.

The present process produces the desired peroxycarboxylic acid upon combining the reaction components. The reaction components may remain separated until use.

In a further aspect, a peroxycarboxylic acid generation and delivery system is provided comprising:

(a) a first compartment comprising
  (1) an enzyme catalyst comprising a polypeptide having perhydrolytic activity and an amino acid sequence having at least 80% identity to the amino acid sequence set forth in SEQ ID NO: 10 provided that the amino acid residue bound to the C-terminal side of the catalytic histidine is not glutamic acid;
  (2) at least one substrate selected from the group consisting of:
    (i) one or more esters having the structure $[X]_mR_5$ wherein
X=an ester group of the formula $R_6$—C(O)O;
$R_6$=a C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m=an integer ranging from 1 to the number of carbon atoms in $R_5$; and wherein said esters have solubility in water of at least 5 ppm at 25° C.;

(ii) one or more glycerides having the structure

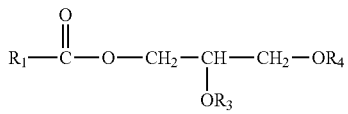

wherein $R_1$=a C1 to C21 straight chain or branched chain alkyl optionally substituted with an hydroxyl or a C1 to C4 alkoxy group and $R_3$ and $R_4$ are individually H or $R_1C(O)$;

(iii) one or more esters of the formula:

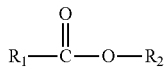

wherein $R_1$=a C1 to C7 straight chain or branched chain alkyl optionally substituted with an hydroxyl or a C1 to C4 alkoxy group and $R_2$=a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10;

(iv) one or more acylated monosaccharides, acylated disaccharides, or acylated polysaccharides; and (v) any combination of (i) through (iv); and (3) an optional buffer; and (b) a second compartment comprising (1) source of peroxygen;

(2) a peroxide stabilizer; and (3) an optional buffer.

In a further embodiment, a laundry care composition is provided comprising a) a polypeptide having perhydrolytic activity and an amino acid sequence having at least 80% identity to the amino acid sequence set forth in SEQ ID NO: 10, provided that the amino acid residue bound to the C-terminal side of the catalytic histidine is not glutamic acid;

b) at least one substrate selected from the group consisting of:

(i) one or more esters having the structure $[X]_mR_5$ wherein

X=an ester group of the formula $R_6$—C(O)O;

$R_6$=a C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m=an integer ranging from 1 to the number of carbon atoms in $R_5$; and wherein said esters have solubility in water of at least 5 ppm at 25° C.;

(ii) one or more glycerides having the structure

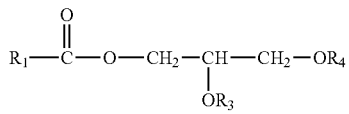

wherein $R_1$=a C1 to C21 straight chain or branched chain alkyl optionally substituted with an hydroxyl or a C1 to C4 alkoxy group and $R_3$ and $R_4$ are individually H or $R_1C(O)$;

(iii) one or more esters of the formula:

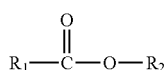

wherein $R_1$=a C1 to C7 straight chain or branched chain alkyl optionally substituted with an hydroxyl or a C1 to C4 alkoxy group and $R_2$=a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10;

(iv) one or more acylated monosaccharides, acylated disaccharides, or acylated polysaccharides; and (v) any combination of (i) through (iv); and c) a source of peroxygen; and d) at least one surfactant.

In a further embodiment, a personal care product is provided comprising a polypeptide having perhydrolytic activity, said polypeptide having an amino acid sequence having at least 80% identity to the amino acid sequence set forth in SEQ ID NO: 10, provided that the amino acid residue bound to the C-terminal side of the catalytic histidine is not glutamic acid.

In a further embodiment, the personal care product is a shampoo, a body lotion, a shower gel, a topical moisturizer, a toothpaste, a toothgel, a mouthwash, a mouthrinse, an antiplaque rinse or a topical cleanser.

BRIEF DESCRIPTION OF THE FIGURE

FIG. 1A-1B is a CLUSTALW alignment of SEQ ID NOs: 2, 4, 6, 8, 10, and 12. Underlining indicates the three conserved submotifs of the CE-7 esterase signature motif.

BRIEF DESCRIPTION OF THE BIOLOGICAL SEQUENCES

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST. 25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the nucleic acid sequence of the codon-optimized coding region encoding the *Thermotoga maritima* acetyl xylan esterase having perhydrolytic activity.

SEQ ID NO: 2 is the amino acid sequence of the *Thermotoga maritima* acetyl xylan esterase having perhydrolytic activity.

SEQ ID NO: 3 is the nucleic acid sequence of the codon-optimized coding region encoding an *Actinosynnema mirum* acetyl xylan esterase having perhydrolytic activity.

SEQ ID NO: 4 is the amino acid sequence of an *Actinosynnema mirum* acetyl xylan esterase having perhydrolytic activity.

SEQ ID NO: 5 is the nucleic acid sequence of the codon-optimized coding region encoding a *Propionibacterium acnes* acetyl xylan esterase having perhydrolytic activity.

SEQ ID NO: 6 is the amino acid sequence of a *Propionibacterium acnes* acetyl xylan esterase having perhydrolytic activity.

SEQ ID NO: 7 is the nucleic acid sequence of the codon-optimized coding region encoding a *Streptococcus equi* acetyl xylan esterase having perhydrolytic activity.

SEQ ID NO: 8 is the amino acid sequence of a *Streptococcus equi* acetyl xylan esterase having perhydrolytic activity.

SEQ ID NO: 9 is the nucleic acid sequence of the codon-optimized coding region encoding a *Stackebrandtia nassauensis* acetyl xylan esterase having perhydrolytic activity.

SEQ ID NO: 10 is the amino acid sequence of a *Stackebrandtia nassauensis* acetyl xylan esterase having perhydrolytic activity.

SEQ ID NO: 11 is the nucleic acid sequence of the codon-optimized coding region encoding a *Streptococcus agalactiae* acetyl xylan esterase having perhydrolytic activity.

SEQ ID NO: 12 is the amino acid sequence of a *Streptococcus agalactiae* acetyl xylan esterase having perhydrolytic activity.

SEQ ID NO: 13 is the nucleic acid sequence of the codon-optimized coding region encoding an *Actinosynnema mirum* C277S variant acetyl xylan esterase having perhydrolytic activity.

SEQ ID NO: 14 is the amino acid sequence of an *Actinosynnema mirum* C277S variant acetyl xylan esterase having perhydrolytic activity.

SEQ ID NO: 15 is the nucleic acid sequence of the codon-optimized coding region encoding an *Actinosynnema mirum* C277T variant acetyl xylan esterase having perhydrolytic activity.

SEQ ID NO: 16 is the amino acid sequence of an *Actinosynnema mirum* C277T variant acetyl xylan esterase having perhydrolytic activity.

SEQ ID NO: 17 is the amino acid sequence of the *Thermotoga maritima* variant C277S (U.S. Pat. No. 8,062,875).

SEQ ID NO: 18 is the amino acid sequence of the *Thermotoga maritima* variant C277T (U.S. Pat. No. 8,062,875).

DETAILED DESCRIPTION

Compositions and methods are provided comprising a polypeptide having perhydrolytic activity, the polypeptide having an amino acid sequence having at least 80% identity to the amino acid sequence set forth in SEQ ID NO: 10, provided that the amino acid residue bound to the C-terminal side of the catalytic histidine is not glutamic acid. The compositions and methods are suitable to enzymatically produce at least one peracid suitable for use in a laundry care product, a disinfectant product, a cosmetic product or a personal care product.

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

The term "comprising" means the presence of the stated features, integers, steps, or components as referred to in the claims, but does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "multi-component system" will refer to a system of enzymatically generating peroxycarboxylic acid wherein the components remain separated until use. As such, the multi-component system will include at least one first component that remains separated from at least one second component. The first and second components are separated in different compartments until use (i.e., using first and second compartments). The design of the multi-component systems will often depend on the physical form of the components to be combined and are described in more detail below.

As used herein, the term "peroxycarboxylic acid" is synonymous with peracid, peroxyacid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate; 1,2,3-triacetoxpropane; 1,2,3-propanetriol triacetate; and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate; 1,2,3-tributyrylglycerol; and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the terms "acylated sugar" and "acylated saccharide" refer to mono-, di- and polysaccharides comprising at least one acyl group, where the acyl group is selected from the group consisting of straight chain aliphatic carboxylates having a chain length from C2 to C8. Examples include, but are not limited to, glucose pentaacetate, xylose tetraacetate, acetylated xylan, acetylated xylan fragments, β-D-ribofuranose-1,2,3,5-tetraacetate, tri-O-acetyl-D-galactal, and tri-O-acetyl-glucal.

As used herein, the terms "hydrocarbyl", "hydrocarbyl group", and "hydrocarbyl moiety" mean a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In one embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the term "aromatic" refers to an organic compound or moiety characterized by increased chemical stability resulting from the delocalization of electrons in a ring system containing usually multiple conjugated double bonds. Planar monocyclic conjugated rings having delocalized electrons should be aromatic if the have (4n+2) π electrons. Examples of aromatic compounds may include derivatives of benzene (such as 2-, 3- or 4-acetoxybenzoic acid). In one embodiment, the ester substrate may be 4-acetoxybenzoic acid.

As used herein, the term "heterocyclic" refers to an organic compound or moiety with a ring structure having one or more atoms other than carbon in at least one of its rings.

As used herein, the term "heteroaromatic" refers to an organic compound or moiety with a ring structure that is both heterocyclic and aromatic, wherein the ring comprises at least one of the heteroatoms oxygen, nitrogen, or sulfur. Examples of heteroaromatic moieties may include pyridine, pyrrole, furan, and thiophene moieties.

As used herein, the terms "monoesters" and "diesters" of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol, refer to said compounds comprising at least one ester group of the formula RC(O)O, wherein R is a C1 to C7 linear hydrocarbyl moiety.

As used herein, the terms "suitable enzymatic reaction formulation", "components suitable for generation of a peroxycarboxylic acid", "suitable reaction components", "reaction components", "reaction formulation", and "suitable aqueous reaction formulation" refer to the materials and water in which the reactants and the enzyme catalyst comprising the present variant polypeptide having perhydrolytic activity come into contact to form the desired peroxycarboxylic acid. The components of the reaction formulation are provided herein and those skilled in the art appreciate the range of component variations suitable for this process. In one embodiment, the enzymatic reaction formulation produces peroxycarboxylic acid in situ upon combining the reaction components. As such, the reaction components may be provided as a multi-component system wherein one or more of the reaction components remains separated until use. The design of systems and means for separating and combining multiple active components are known in the art and generally will depend upon the physical form of the individual reaction components. For example, multiple active fluids (liquid-liquid) systems typically use multi-chamber dispenser bottles or two-phase systems (U.S. Patent Application Publication No. 2005-0139608; U.S. Pat. No. 5,398,846; U.S. Pat. No. 5,624,634; U.S. Pat. No. 6,391,840; E.P. Patent 0807156B1; U.S. Patent Application Publication No. 2005-0008526; and PCT Publication No. WO 00/61713) such as found in some bleaching applications wherein the desired bleaching agent is produced upon mixing the reactive fluids. Multi-component formulations and multi-component generation systems to enzymatically produce peroxycarboxylic acids from carboxylic acid esters are described by DiCosimo et al. in Published U.S Patent Application Nos. 2010-0086510 and 2010-0086621, respectively. Other forms of multi-component systems used to generate peroxycarboxylic acid may include, but are not limited to, those designed for one or more solid components or combinations of solid-liquid components, such as powders used in many commercially available bleaching compositions (e.g., U.S. Pat. No. 5,116,575), multi-layered tablets (e.g., U.S. Pat. No. 6,210,639), water dissolvable packets having multiple compartments (e.g., U.S. Pat. No. 6,995,125) and solid agglomerates that react upon the addition of water (e.g., U.S. Pat. No. 6,319,888).

As used herein, the term "substrate" or "carboxylic acid ester substrate" will refer to the reaction components enzymatically perhydrolyzed using the present enzyme catalyst in the presence of a suitable source of peroxygen, such as hydrogen peroxide. In one embodiment, the substrate comprises at least one ester group capable of being enzymatically perhydrolyzed using the enzyme catalyst, whereby a peroxycarboxylic acid is produced.

As used herein, the term "perhydrolysis" is defined as the reaction of a selected substrate with a source of hydrogen peroxide to form a peroxycarboxylic acid. Typically, inorganic peroxide is reacted with the selected substrate in the presence of a catalyst to produce the peroxycarboxylic acid. As used herein, the term "chemical perhydrolysis" includes perhydrolysis reactions in which a substrate (such as a peroxycarboxylic acid precursor) is combined with a source of hydrogen peroxide wherein peroxycarboxylic acid is formed in the absence of an enzyme catalyst. As used herein, the term "enzymatic perhydrolysis" refers a reaction of a selected substrate with a source of hydrogen peroxide to form a peroxycarboxylic acid, wherein the reaction is catalyzed by an enzyme catalyst having perhydrolysis activity.

As used herein, the term "perhydrolase activity" refers to the enzyme catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 µmol of peroxycarboxylic acid product (such as peracetic acid) per minute at a specified temperature. "One unit of enzyme activity" may also be used herein to refer to the amount of peroxycarboxylic acid hydrolysis activity required for the hydrolysis of 1 µmol of peroxycarboxylic acid (e.g., peracetic acid) per minute at a specified temperature.

As used herein, the terms "enzyme catalyst" and "perhydrolase catalyst" refer to a catalyst comprising an enzyme (i.e., a polypeptide) having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (for example, by pegylation or by reaction with cross-linking reagents). The perhydrolase catalyst may also be immobilized on a soluble or insoluble support using methods well-known to those skilled in the art; see for example, *Immobilization of Enzymes and Cells*; ($2^{nd}$ Edition) Jose M. Guisan, Editor; Humana Press, Totowa, N.J., USA; 2006.

As used herein, "structurally classified as a CE-7 enzyme", "structurally classified as a carbohydrate esterase family 7 enzyme", "structurally classified as a CE-7 carbohydrate esterase", and "CE-7 perhydrolase" will be used herein to refer to enzymes having perhydrolysis activity that are structurally classified as a CE-7 carbohydrate esterase (see Cantarel et al., "The Carbohydrate-Active EnZymes database (CAZy): an expert resource for Glycogenomics", *NAR*, 37:D233-D238 (2009)).

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima et al., *Appl. Environ. Microbiol.*, 61(6): 2224-2229 (1995); U.S. Pat. No. 5,528,152; and U.S. Pat. No. 5,338,676).

As used herein, "acetyl xylan esterase" refers to an enzyme (E.C. 3.1.1.72; AXEs) that catalyzes the deacetylation of acetylated xylans and other acetylated saccharides.

As used herein, the term "*Thermotoga maritima*" refers to a bacterial cell reported to have acetyl xylan esterase activity (GENBANK® NP_227893.1). In one aspect, the *Thermotoga maritima* strain is *Thermotoga maritima* MSB8. The amino acid sequence of the wild-type enzyme having perhydrolase activity from *Thermotoga maritima* is provided as SEQ ID NO: 2.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid (or as defined herein) | Xaa | X |

As used herein, the term "biological contaminants" refers to one or more unwanted and/or pathogenic biological entities including, but not limited to, microorganisms, spores, viruses, prions, and mixtures thereof. The present enzyme can be used to produce an efficacious concentration of at least one peroxycarboxylic acid useful to reduce and/or eliminate the presence of the viable biological contaminants. In a preferred embodiment, the biological contaminant is a viable pathogenic microorganism.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. Typically, disinfectants are used to treat inanimate objects or surfaces. As used herein, the term "antiseptic" refers to a chemical agent that inhibits the growth of disease-carrying microorganisms. In one aspect of the embodiment, the biological contaminants are pathogenic microorganisms.

As used herein, the term "sanitary" means of or relating to the restoration or preservation of health, typically by removing, preventing or controlling an agent that may be injurious to health. As used herein, the term "sanitize" means to make sanitary. As used herein, the term "sanitizer" refers to a sanitizing agent. As used herein the term "sanitization" refers to the act or process of sanitizing.

As used herein, the term "virucide" refers to an agent that inhibits or destroys viruses, and is synonymous with "viricide". An agent that exhibits the ability to inhibit or destroy viruses is described as having "virucidal" activity. Peroxycarboxylic acids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peroxycarboxylic acids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is at least a 3–$\log_{10}$ reduction, more preferably at least a 4–$\log_{10}$ reduction, and most preferably at least a 5–$\log_{10}$ reduction. In another aspect, the minimum biocidal concentration is at least a 6–$\log_{10}$ reduction in viable microbial cells.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates, such as sodium percarbonate. As described herein, the concentration of the hydrogen peroxide provided by the peroxygen compound in the aqueous reaction formulation is initially at least 1 mM or more upon combining the reaction components. In one embodiment, the hydrogen peroxide concentration in the aqueous reaction formulation is at least 0.5 mM. In another embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, such as triglyceride, ($H_2O_2$:substrate) in the aqueous reaction formulation may be from about 0.002 to 20, preferably about 0.1 to 10, and most preferably about 0.5 to 5.

As used herein, the term "benefit agent" refers to a material that promotes or enhances a useful advantage, a favorable/desirable effect or benefit. In one embodiment, a process is provided whereby a benefit agent, such as a composition comprising a peroxycarboxylic acid, is applied to a textile or article of clothing to achieve a desired benefit, such as disinfecting, bleaching, destaining, deodorizing, and any combination thereof. In another embodiment, the present variant polypeptide having perhydrolytic activity may be used to produce a peracid-based benefit agent for use in personal care products (such as hair care products, skin care products, nail care products or oral care products). In one embodiment, a personal care product is provided comprising a polypeptide having perhydrolytic activity, said polypeptide having an amino acid sequence having at least 80% identity to the amino acid sequence set forth in SEQ ID NO: 10, provided that the amino acid residue bound to the C-terminal side of the catalytic histidine is not glutamic acid. The personal care products are formulated to provide a safe and efficacious concentration of the desired peracid benefit agent.

As used herein, "personal care products" means products used in the cleaning, bleaching and/or disinfecting of hair, skin, scalp, and teeth, including, but not limited to, shampoos, body lotions, shower gels, topical moisturizers, toothpaste, toothgels, mouthwashes, mouthrinses, anti-plaque rinses, and/or other topical cleansers. In some particularly preferred embodiments, these products are utilized on humans, while in other embodiments, these products find use with non-human animals (e.g., in veterinary applications).

As used herein, the terms "tooth whitening" and "tooth bleaching" are used interchangeably, to refer to improving the brightness (e.g., whitening) of a tooth or teeth. It is intended that the term encompass any method suitable for whitening teeth, including the present invention, as well as chemical treatment, mild acid treatment, abrasive tooth whitening, and laser tooth whitening. In particularly preferred embodiments, the present invention provides a perhydrolase and perhydrolase-containing compositions suitable for whitening teeth.

Polypeptides Having Perhydrolytic Activity

The "signature motif" for CE-7 esterases previously reported to have perhydrolytic activity is comprised three conserved submotifs (residue position numbering relative to reference sequence SEQ ID NO: 2; the wild-type *Thermotoga maritima* acetyl xylan esterase):

a) Arg118-Gly119-Gln120; ("RGQ motif");

b) Gly186-Xaa187-Ser188-Gln189-Gly190; and ("GXSQG motif"); and c) His303-Glu304. ("HE motif").

Typically, the Xaa at amino acid residue position 187 is glycine, alanine, proline, tryptophan, or threonine. Two of the three amino acid residues belonging to the catalytic triad are in bold.

Although the present perhydrolytic enzymes contain the RGQ motif and the GXSQG motif, none of the present perhydrolytic enzymes contain the glutamic acid within the "HE motif" previously reported as a conserved structural motif as shown in Table A and FIG. 1.

TABLE A

Motifs found within the present enzymes having perhydrolase activity.

| Perhydrolase Sequence | RGQ motif (Residue #s) | GXSQG motif (Residue #s) | HX motif (Residue #s) | Amino acid residue bound to catalytic histidine in HX motif |
|---|---|---|---|---|
| SEQ ID NO: 2[a] | 118-120 | 186-190 | 303-304 | E[b] |
| SEQ ID NO: 4 | 118-120 | 184-188 | 302-303 | A |
| SEQ ID NO: 6 | 117-119 | 184-188 | 309-310 | A |
| SEQ ID NO: 8 | 114-116 | 177-181 | 299-300 | D |
| SEQ ID NO: 10 | 117-119 | 186-190 | 303-304 | S |
| SEQ ID NO: 12 | 115-117 | 178-182 | 299-300 | D |
| SEQ ID NO: 14 | 118-120 | 184-188 | 302-303 | A |
| SEQ ID NO: 16 | 118-120 | 184-188 | 302-303 | A |

[a]=*Thermotoga maritima* reference sequence.
[b]=Previously reported to be a conserved glutamic acid, forming an "HE" motif.

It appears the present polypeptides having perhydrolytic activity may represent a new subgroup within the larger generic class of CE-7 carbohydrate esterases listed as members within the CAZy database (Cantarel et al., "The Carbohydrate-Active EnZymes database (CAZy): an expert resource for Glycogenomics", *NAR*, 37:D233-D238 (2009)). As such, the polypeptides having perhydrolytic activity used within the present application will be referred to herein as "CE-7 carbohydrate esterases" or "CE-7 perhydrolases" even though they may lack a portion of the previously defined "signature motif".

In another embodiment, the present polypeptides having perhydrolytic activity are further defined as having the following combination of motifs when aligned against reference sequence SEQ ID NO: 2 (residue position numbering relative to reference sequence SEQ ID NO: 2; the wild-type *Thermotoga maritima* acetyl xylan esterase):

a) Arg118-Gly119-Gln120; ("RGQ motif");
b) Gly186-Xaa187-Ser188-Gln189-Gly190; and ("GXSQG motif"); and
c) His303-Xaa304. ("HX motif"); wherein "Xaa" is not glutamic acid.

In a preferred aspect, "X" amino acid residue within the "HX motif" is alanine, aspartic acid, or serine.

In another aspect, the present polypeptide having perhydrolytic activity comprises an amino acid sequence having at least 80% identity to an amino acid sequence selected from the group consisting of SEQ ID NOs: 4, 6, 8, 10, 12, 14, and 16, provided that the amino acid residue bound to the C-terminal side of the catalytic histidine is not glutamic acid.

In one embodiment, the present polypeptides having perhydrolytic activity have at least 70, 71, 72, 73, 74, 75, 76, 77, 78, 79, 80, 81, 82, 83, 84, 84, 86, 87, 88, 89, 90, 91, 92, 93, 94, 95, 96, 97, 98, 99 or 100% amino acid identity to the sequences provided herein, provided that the amino acid residue bound to the C-terminal side of the catalytic histidine is not glutamic acid.

In another aspect, the present polypeptide having perhydrolytic activity comprises an amino acid sequence having at least 80% identity to an amino acid sequence having at least 80% identity to the amino acid sequence set forth in SEQ ID NO: 10, provided that the amino acid residue bound to the C-terminal side of the catalytic histidine is not glutamic acid. In another aspect, the present polypeptide having perhydrolytic activity comprises an amino acid sequence SEQ ID NO: 10.

As used herein, the term "variant perhydrolase" or "variant" will refer to perhydrolytic enzymes having a modification that results in at least one amino acid addition, deletion, and/or substitution when compared to the corresponding enzyme (typically the wild type enzyme) from which the variant was derived; so long as the requisite motifs described herein and the associated perhydrolytic activity are maintained. CE-7 variant perhydrolases may also be used in the present compositions and methods. Examples of variants are provided as SEQ ID NOs: 14 and 16.

The skilled artisan recognizes that substantially similar perhydrolase sequences may also be used in the present compositions and methods. In one embodiment, substantially similar sequences are defined by their ability to hybridize, under highly stringent conditions, with the nucleic acid molecules associated with sequences exemplified herein. In another embodiment, sequence alignment algorithms may be used to define substantially similar enzymes based on the percent identity to the DNA or amino acid sequences provided herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D. T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of highly stringent hybridization conditions is 0.1×SSC, 0.1% SDS, 65° C. and washed with 2×SSC, 0.1% SDS followed by a final wash of 0.1×SSC, 0.1% SDS, 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the CLUSTAL method (such as CLUSTALW; for example version 1.83) of alignment (Higgins and Sharp, *CABIOS*, 5:151-153 (1989); Higgins et al., *Nucleic Acids Res.* 22:4673-4680 (1994); and Chema et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein END-GAP=−1, protein GAPDIST=4, and KTUPLE=1. In one embodiment, a fast or slow alignment is used with the default settings where a slow alignment is preferred. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

By "catalytic histidine" is meant the histidine residue in the presently disclosed perhydrolases that forms a catalytic triad with serine and aspartic acid. For example, in SEQ ID NO: 10, the catalytic histidine is amino acid residue number 303. A variant of SEQ ID NO: 10 that has perhydrolase activity will have its catalytic histidine align with the catalytic histidine of SEQ ID NO: 10 when the sequences are compared using CLUSTALW, meaning that the variant's catalytic histidine may, but does not have to be, at amino acid position 303 of the variant.

In one aspect, suitable isolated nucleic acid molecules encode a polypeptide having an amino acid sequence that is at least 70, 71, 72, 73, 74, 75, 76, 77, 78, 79, 80, 81, 82, 83, 84, 84, 86, 87, 88, 89, 90, 91, 92, 93, 94, 95, 96, 97, 98, or 99% identical to the amino acid sequences reported herein. Suitable nucleic acid molecules not only have the above homologies, but also typically encode a polypeptide having about 210 to 340 amino acids in length, about 300 to about 340 amino acids, preferably about 310 to about 330 amino acids, and most preferably about 318 to about 325 amino acids in length wherein each polypeptide is characterized as having perhydrolytic activity.

Suitable Reaction Conditions for the Enzyme-Catalyzed Preparation of Peroxycarboxylic Acids from Carboxylic Acid Esters and Hydrogen Peroxide A process is provided to produce an aqueous formulation comprising at least one peroxycarboxylic acid by reacting carboxylic acid esters and an inorganic peroxide (such as hydrogen peroxide, sodium perborate or sodium percarbonate) in the presence of an enzyme catalyst having perhydrolysis activity, wherein the enzyme catalyst comprises, in one embodiment, a polypeptide having at least 80% identity to an amino acid sequence selected from the group consisting of SEQ ID NOs: 4, 6, 8, 10, 12, 14, and 16, provided that the amino acid residue bound to the C-terminal side of the catalytic histidine is not glutamic acid. In a further embodiment, the polypeptide having perhydrolytic activity comprises an amino acid sequence selected from SEQ ID NOs: 4, 6, 8, 10, 12, 14, and 16. In a further embodiment, the polypeptide has the amino acid sequence of SEQ ID NO: 10.

In one embodiment, suitable substrates include one or more esters provided by the following formula:

wherein X=an ester group of the formula $R_6C(O)O$ $R_6$=a C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m=an integer ranging from 1 to the number of carbon atoms in $R_5$; and wherein said esters have solubility in water of at least 5 ppm at 25° C.

In another embodiment, $R_6$=a C1 to C7 linear hydrocarbyl moiety, optionally substituted with hydroxyl groups or C1 to C4 alkoxy groups, optionally comprising one or more ether linkages. In a further preferred embodiment, $R_6$=a C2 to C7 linear hydrocarbyl moiety, optionally substituted with hydroxyl groups, and/or optionally comprising one or more ether linkages.

In one embodiment, the suitable substrate may include 2-acetoxybenzoic acid, 3-acetoxybenzoic acid, 4-acetoxybenzoic acid or mixtures thereof.

In another embodiment, suitable substrates also include one or more glycerides of the formula:

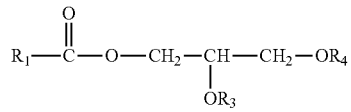

wherein $R_1$=a C1 to C21 straight chain or branched chain alkyl optionally substituted with an hydroxyl or a C1 to C4 alkoxy group and $R_3$ and $R_4$ are individually H or $R_1C(O)$. In one embodiment, the suitable substrate is a glyceride of the above formula wherein $R_1$=a C1 to C7 straight chain or branched chain alkyl optionally substituted with an hydroxyl or a C1 to C4 alkoxy group and $R_3$ and $R_4$ are individually H or $R_1C(O)$.

In another aspect, suitable substrates may also include one or more esters of the formula:

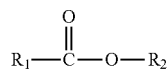

wherein $R_1$=a C1 to C7 straight chain or branched chain alkyl optionally substituted with an hydroxyl or a C1 to C4 alkoxy group and $R_2$=a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)$—$O)_nH$ and n is 1 to 10.

Suitable substrates may also include one or more acylated saccharides selected from the group consisting of acylated mono-, di-, and polysaccharides. In another embodiment, the acylated saccharides are selected from the group consisting of acetylated xylan, fragments of acetylated xylan, acetylated xylose (such as xylose tetraacetate), acetylated glucose (such as α-D-glucose pentaacetate; β-D-glucose pentaacetate), β-D-galactose pentaacetate, sorbitol hexaacetate, sucrose octaacetate, β-D-ribofuranose-1,2,3,5-tetraacetate, tri-O-acetyl-D-galactal, tri-O-acetyl-D-glucal, tetraacetylxylofuranose, α-D-glucopyranose pentaacetate, α-D-mannopyranose pentaacetate, and acetylated cellulose. In a preferred embodiment, the acetylated saccharide is selected from the group consisting of β-D-ribofuranose-1,2,3,5-tetraacetate, tri-O-acetyl-D-galactal, tri-O-acetyl-D-glucal, sucrose octaacetate, and acetylated cellulose.

In another embodiment, suitable substrates are selected from the group consisting of: monoacetin; diacetin; triacetin;

monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-D-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

In another embodiment, the carboxylic acid ester is selected from the group consisting of monoacetin, diacetin, triacetin, and combinations thereof. In another embodiment, the substrate is a C1 to C6 polyol comprising one or more ester groups. In a preferred embodiment, one or more of the hydroxyl groups on the C1 to C6 polyol are substituted with one or more acetoxy groups (such as 1,3-propanediol diacetate, 1,4-butanediol diacetate, etc.). In a further embodiment, the substrate is propylene glycol diacetate (PGDA), ethylene glycol diacetate (EGDA), or a mixture thereof.

In another embodiment, suitable substrates are selected from the group consisting of ethyl acetate; methyl lactate; ethyl lactate; methyl glycolate; ethyl glycolate; methyl methoxyacetate; ethyl methoxyacetate; methyl 3-hydroxybutyrate; ethyl 3-hydroxybutyrate; triethyl 2-acetyl citrate; glucose pentaacetate; gluconolactone; glycerides (mono-, di-, and triglycerides) such as monoacetin, diacetin, triacetin, monopropionin, dipropionin (glyceryl dipropionate), tripropionin (1,2,3-tripropionylglycerol), monobutyrin, dibutyrin (glyceryl dibutyrate), tributyrin (1,2,3-tributyrylglycerol); acetylated saccharides; and mixtures thereof.

In a further embodiment, suitable substrates are selected from the group consisting of monoacetin, diacetin, triacetin, monopropionin, dipropionin, tripropionin, monobutyrin, dibutyrin, tributyrin, ethyl acetate, and ethyl lactate. In yet another aspect, the substrate is selected from the group consisting of diacetin, triacetin, ethyl acetate, and ethyl lactate. In a most preferred embodiment, the suitable substrate comprises triacetin.

The carboxylic acid ester is present in the aqueous reaction formulation at a concentration sufficient to produce the desired concentration of peroxycarboxylic acid upon enzyme-catalyzed perhydrolysis. The carboxylic acid ester need not be completely soluble in the aqueous reaction formulation, but has sufficient solubility to permit conversion of the ester by the perhydrolase catalyst to the corresponding peroxycarboxylic acid. The carboxylic acid ester is present in the aqueous reaction formulation at a concentration of 0.0005 wt % to 40 wt % of the aqueous reaction formulation, preferably at a concentration of 0.01 wt % to 20 wt % of the aqueous reaction formulation, and more preferably at a concentration of 0.05 wt % to 10 wt % of the aqueous reaction formulation. The wt % of carboxylic acid ester may optionally be greater than the solubility limit of the carboxylic acid ester, such that the concentration of the carboxylic acid ester is at least 0.0005 wt % in the aqueous reaction formulation that is comprised of water, enzyme catalyst, and source of peroxide, where the remainder of the carboxylic acid ester remains as a second separate phase of a two-phase aqueous/organic reaction formulation. Not all of the added carboxylic acid ester must immediately dissolve in the aqueous reaction formulation, and after an initial mixing of all reaction components, additional continuous or discontinuous mixing is optional.

The peroxycarboxylic acids produced by the present reaction components may vary depending upon the selected substrates, so long as the present enzyme catalyst is used. In one embodiment, the peroxycarboxylic acid produced is peracetic acid, perpropionic acid, perbutyric acid, peroctanoic acid, perlactic acid, perglycolic acid, permethoxyacetic acid, per-β-hydroxybutyric acid, or mixtures thereof.

The peroxygen source may include, but is not limited to, hydrogen peroxide, hydrogen peroxide adducts (e.g., urea-hydrogen peroxide adduct (carbamide peroxide)), perborate salts and percarbonate salts. Alternatively, hydrogen peroxide can be generated in situ by the reaction of a substrate and oxygen catalyzed by an enzyme having oxidase activity (including, but not limited to, glucose oxidase, galactose oxidase, sorbitol oxidase, hexose oxidase, alcohol oxidase, glycerol oxidase, monoamine oxidase, glycolate oxidase, lactate oxidase, pyruvate oxidase, oxalate oxidase, choline oxidase, cholesterol oxidase, pyranose oxidase, carboxyalcohol oxidase, L-amino acid oxidase, glycine oxidase, glutamate oxidase, lysine oxidase, and uricase). The concentration of peroxygen compound in the aqueous reaction formulation may range from 0.0033 wt % to about 50 wt %, preferably from 0.033 wt % to about 40 wt %, more preferably from 0.33 wt % to about 30 wt %.

Many perhydrolase catalysts (such as whole cells, permeabilized whole cells, and partially purified whole cell extracts) have been reported to have catalase activity (EC 1.11.1.6). Catalases catalyze the conversion of hydrogen peroxide into oxygen and water. In one aspect, the enzyme catalyst having perhydrolase activity lacks catalase activity. In another aspect, the enzyme catalyst having perhydrolase activity has a sufficiently-low catalase activity that the presence of said catalase activity does not significantly interfere with perhydrolase-catalyzed peroxycarboxylic acid production. In another aspect, a catalase inhibitor is added to the aqueous reaction formulation. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM.

The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e., "knocked-out"). As used herein, a "disrupted" gene is one where the activity and/or function of the protein encoded by the modified gene are no longer present. Means to disrupt a gene are well-known in the art and may include, but are not limited to, insertions, deletions, or mutations to the gene so long as the activity and/or function of the corresponding protein is no longer present. In a further preferred embodiment, the production host is an *E. coli* production host comprising a disrupted catalase gene selected from the group consisting of katG and katE (see U.S. Pat. No. 7,951,566 to DiCosimo et al.). In another embodiment, the production host is an *E. coli* strain comprising a down-regulation and/or disruption in both katG and katE catalase genes. An *E. coli* strain comprising a double-knockout of katG and katE has been prepared and is described as *E. coli* strain KLP18 (U.S. Pat. No. 7,951,566 to DiCosimo et al.).

The concentration of the catalyst in the aqueous reaction formulation depends on the specific catalytic activity of the catalyst, and is chosen to obtain the desired rate of reaction. The weight of catalyst in perhydrolysis reactions typically ranges from 0.0001 mg to 50 mg per mL of total reaction volume, preferably from 0.0005 mg to 10 mg per mL, more preferably from 0.0010 mg to 2.0 mg per mL. The catalyst may also be immobilized on a soluble or insoluble support using methods well-known to those skilled in the art; see for example, *Immobilization of Enzymes and Cells (2$^{nd}$ Edition)*; Jose M. Guisan, Editor; Humana Press, Totowa, N.J., USA; 2006. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peroxycarboxylic acid generated by the combination of chemical perhydrolysis and enzymatic perhydrolysis of the carboxylic acid ester is sufficient to provide an effective concentration of peroxycarboxylic acid for disinfection, bleaching, sanitization, deodorizing or destaining at a desired pH. In another aspect, the peroxycarboxylic acid is generated at a safe and efficacious concentration suitable for use in a personal care product to be applied to the hair, skin, nails or tissues of the oral cavity, such as tooth enamel, tooth pellicle or the gums. In another aspect, the present methods provide combinations of enzymes and enzyme substrates to produce the desired effective concentration of peroxycarboxylic acid, where, in the absence of added enzyme, there is a significantly lower concentration of peroxycarboxylic acid produced. Although there may be some chemical perhydrolysis of the enzyme substrate by direct chemical reaction of inorganic peroxide with the enzyme substrate, there may not be a sufficient concentration of peroxycarboxylic acid generated to provide an effective concentration of peroxycarboxylic acid in the desired applications, and a significant increase in total peroxycarboxylic acid concentration is achieved by the addition of an appropriate perhydrolase catalyst to the aqueous reaction formulation.

In one aspect of the invention, the concentration of peroxycarboxylic acid generated (e.g. peracetic acid) by the enzymatic perhydrolysis is at least about 2 ppm, preferably at least 20 ppm, preferably at least 100 ppm, more preferably at least about 200 ppm peroxycarboxylic acid, more preferably at least 300 ppm, more preferably at least 500 ppm, more preferably at least 700 ppm, more preferably at least about 1000 ppm peroxycarboxylic acid, more preferably at least about 2000 ppm peroxycarboxylic acid, most preferably at least 10,000 ppm peroxycarboxylic acid within 5 minutes more preferably within 1 minute of initiating the enzymatic perhydrolysis reaction. In a second aspect of the invention, the concentration of peroxycarboxylic acid generated (e.g. peracetic acid) by the enzymatic perhydrolysis is at least about 2 ppm, preferably at least 20 ppm, preferably at least 30 ppm, more preferably at least about 40 ppm peroxycarboxylic acid, more preferably at least 50 ppm, more preferably at least 60 ppm, more preferably at least 70 ppm, more preferably at least about 80 ppm peroxycarboxylic acid, most preferably at least 100 ppm peroxycarboxylic acid within 5 minutes, more preferably within 1 minute, of initiating the enzymatic perhydrolysis reaction (i.e., time measured from combining the reaction components to form the formulation).

The aqueous formulation comprising the peroxycarboxylic acid may be optionally diluted with diluent comprising water, or a solution predominantly comprised of water, to produce a formulation with the desired lower target concentration of peroxycarboxylic acid. In one aspect, the reaction time required to produce the desired concentration (or concentration range) of peroxycarboxylic acid is about 20 minutes or less, preferable about 5 minutes or less, most preferably about 1 minute or less.

In other aspects, the surface or inanimate object contaminated with a concentration of a biological contaminant(s) is contacted with the peroxycarboxylic acid formed in accordance with the processes described herein within about 1 minute to about 168 hours of combining said reaction components, or within about 1 minute to about 48 hours, or within about 1 minute to 2 hours of combining said reaction components, or any such time interval therein.

In another aspect, the peroxycarboxylic acid formed in accordance with the processes describe herein is used in a laundry care application wherein the peroxycarboxylic acid is contacted with clothing or a textile to provide a benefit, such as disinfecting, bleaching, destaining, deodorizing and/or a combination thereof. The peroxycarboxylic acid may be used in a variety of laundry care products including, but not limited to, laundry or textile pre-wash treatments, laundry detergents or additives, stain removers, bleaching compositions, deodorizing compositions, and rinsing agents. In one embodiment, the present process to produce a peroxycarboxylic acid for a target surface is conducted in situ.

In the context of laundry care applications, the term "contacting an article of clothing or textile" means that the article of clothing or textile is exposed to a formulation disclosed herein. To this end, there are a number of formats the formulation may be used to treat articles of clothing or textiles including, but not limited to, liquid, solids, gel, paste, bars, tablets, spray, foam, powder, or granules and can be delivered via hand dosing, unit dosing, dosing from a substrate, spraying and automatic dosing from a laundry washing or drying machine. Granular compositions can also be in compact form; liquid compositions can also be in a concentrated form.

When the formulations disclosed herein are used in a laundry washing machine, the formulation can further contain components typical to laundry detergents. For example, typical components include, but are not limited to, surfactants, bleaching agents, bleach activators, additional enzymes, suds suppressors, dispersants, lime-soap dispersants, soil suspension and anti-redeposition agents, softening agents, corrosion inhibitors, tarnish inhibitors, germicides, pH adjusting agents, non-builder alkalinity sources, chelating agents, organic and/or inorganic fillers, solvents, hydrotropes, optical brighteners, dyes, and perfumes. The formulations disclosed herein can also be used as detergent additive products in solid or liquid form. Such additive products are intended to supplement or boost the performance of conventional detergent compositions and can be added at any stage of the cleaning process.

In connection with the present systems and methods for laundry care where the peracid is generated for one or more of bleaching, stain removal, and odor reduction, the concentration of peracid generated (e.g., peracetic acid) by the perhydrolysis of at least one carboxylic acid ester may be at least about 2 ppm, preferably at least 20 ppm, preferably at least 100 ppm, and more preferably at least about 200 ppm peracid. In connection with the present systems and methods for laundry care where the peracid is generated for disinfection or sanitization, the concentration of peracid generated (e.g., peracetic acid) by the perhydrolysis of at least one carboxylic acid ester may be at least about 2 ppm, more preferably at least 20 ppm, more preferably at least 200 ppm, more preferably at least 500 ppm, more preferably at least 700 ppm, more preferably at least about 1000 ppm peracid, most preferably at least 2000 ppm peracid within 10 minutes, preferably within 5 minutes, and most preferably within 1 minute of initiating the perhydrolysis reaction. The product formulation comprising the peracid may be optionally diluted with water, or a solution predominantly comprised of water, to produce a formulation with the desired lower concentration of peracid. In one aspect of the present methods and systems, the reaction time required to produce the desired concentration of peracid is not greater than about two hours, preferably not greater than about 30 minutes, more preferably not greater than about 10 minutes, even more preferably not greater than about 5 minutes, and most preferably in about 1 minute or less.

The temperature of the reaction is chosen to control both the reaction rate and the stability of the enzyme catalyst activity. The temperature of the reaction may range from just above the freezing point of the aqueous reaction formulation (approximately 0° C.) to about 85° C., with a preferred range of reaction temperature of from about 5° C. to about 75° C.

The pH of the aqueous reaction formulation while enzymatically producing peroxycarboxylic acid is maintained at a pH ranging from about 5.0 to about 10.0, preferably about 6.5 to about 8.5, and yet even more preferably about 6.5 to about 7.5. In one embodiment, the pH of the aqueous reaction formulation ranges from about 6.5 to about 8.5 for at least 30 minutes after combining the reaction components. The pH of the aqueous reaction formulation may be adjusted or controlled by the addition or incorporation of a suitable buffer, including, but not limited to, phosphate, pyrophosphate, bicarbonate, acetate, or citrate. In one embodiment, the buffer is selected from a phosphate buffer, a bicarbonate buffer, or a buffer formed by the combination of hard water (tap water to simulate laundry care applications) and percarbonate (from sodium percarbonate used to generate hydrogen peroxide). The concentration of buffer, when employed, is typically from 0.1 mM to 1.0 M, preferably from 1 mM to 300 mM, most preferably from 10 mM to 100 mM. In another aspect of the present invention, no buffer is added to the reaction mixture while enzymatically producing peroxycarboxylic acid.

In yet another aspect, the enzymatic perhydrolysis aqueous reaction formulation may contain an organic solvent that acts as a dispersant to enhance the rate of dissolution of the carboxylic acid ester in the aqueous reaction formulation. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

In another aspect, the enzymatic perhydrolysis product may contain additional components that provide desirable functionality. These additional components include, but are not limited to, buffers, detergent builders, thickening agents, emulsifiers, surfactants, wetting agents, corrosion inhibitors (e.g., benzotriazole), enzyme stabilizers, and peroxide stabilizers (e.g., metal ion chelating agents). Many of the additional components are well known in the detergent industry (see, for example, U.S. Pat. No. 5,932,532; hereby incorporated by reference). Examples of emulsifiers include, but are not limited to, polyvinyl alcohol or polyvinylpyrrolidone. Examples of thickening agents include, but are not limited to, LAPONITE® RD (synthetic layered silicate), corn starch, PVP, CARBOWAX® (polyethylene glycol and/or methoxypolyethylene glycol), CARBOPOL® (acrylates crosspolymer), CABOSIL®) (synthetic amphormous fumed silicon dioxide), polysorbate 20, PVA, and lecithin. Examples of buffering systems include, but are not limited to, sodium phosphate monobasic/sodium phosphate dibasic; sulfamic acid/triethanolamine; citric acid/triethanolamine; tartaric acid/triethanolamine; succinic acid/triethanolamine; and acetic acid/triethanolamine. Examples of surfactants include, but are not limited to, a) non-ionic surfactants such as block copolymers of ethylene oxide or propylene oxide, ethoxylated or propoxylated linear and branched primary and secondary alcohols, and aliphatic phosphine oxides; b) cationic surfactants such as quaternary ammonium compounds, particularly quaternary ammonium compounds having a C8-C20 alkyl group bound to a nitrogen atom additionally bound to three C1-C2 alkyl groups; c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates; and d) amphoteric and zwitterionic surfactants such as aminocarboxylic acids, aminodicarboxylic acids, alkybetaines, and mixtures thereof. Additional components may include fragrances, dyes, stabilizers of hydrogen peroxide (e.g., metal chelators such as 1-hydroxyethylidene-1,1-diphosphonic acid (DEQUEST® 2010, Solutia Inc., St. Louis, Mo.) and ethylenediaminetetraacetic acid (EDTA)), TURPINAL® SL (etidronic acid), DEQUEST® 0520 (phosphonate), DEQUEST® 0531 (phosphonate), stabilizers of enzyme activity (e.g., polyethylene glycol (PEG)), and detergent builders.

In another aspect, the enzymatic perhydrolysis product may be pre-mixed to generate the desired concentration of peroxycarboxylic acid prior to contacting the surface or inanimate object to be disinfected.

In another aspect, the enzymatic perhydrolysis product is not pre-mixed to generate the desired concentration of peroxycarboxylic acid prior to contacting the surface or inanimate object to be disinfected, but instead, the components of the aqueous reaction formulation that generate the desired concentration of peroxycarboxylic acid are contacted with the surface or inanimate object to be disinfected and/or bleached or destained, generating the desired concentration of peroxycarboxylic acid. In some embodiments, the components of the aqueous reaction formulation combine or mix at the locus. In some embodiments, the reaction components are delivered or applied to the locus and subsequently mix or combine to generate the desired concentration of peroxycarboxylic acid.

Production of Peroxycarboxylic Acids Using a Perhydrolase Catalyst

The peroxycarboxylic acids, once produced, are quite reactive and may decrease in concentration over extended periods of time, depending on variables that include, but are not limited to, temperature and pH. As such, it may be desirable to keep the various reaction components separated, especially for liquid formulations. In one aspect, the hydrogen peroxide source is separate from either the substrate or the perhydrolase catalyst, preferably from both. This can be accomplished using a variety of techniques including, but not limited to, the use of multicompartment chambered dispensers (U.S. Pat. No. 4,585,150) and at the time of use physically combining the perhydrolase catalyst with a source of peroxygen (such as hydrogen peroxide) and the present substrates to initiate the aqueous enzymatic perhydrolysis reaction. The perhydrolase catalyst may optionally be immobilized within the body of reaction chamber or separated (e.g., filtered, etc.) from the reaction product comprising the peroxycarboxylic acid prior to contacting the surface and/or object targeted for treatment. The perhydrolase catalyst may be in a liquid matrix or in a solid form (e.g., powder or tablet) or embedded within a solid matrix that is subsequently mixed with the substrates to initiate the enzymatic perhydrolysis reaction. In a further aspect, the perhydrolase catalyst may be contained within a dissolvable or porous pouch that may be added to the aqueous substrate matrix to initiate enzymatic perhydrolysis. In yet a further aspect, the perhydrolase catalyst may comprise the contents contained within a separate compartment of a dissolvable or porous pouch that has at least one additional compartment for the containment contents comprising the ester substrate and/or source of peroxide. In an additional further aspect, a powder comprising the enzyme catalyst is suspended in the substrate (e.g., triacetin), and at time of use is mixed with a source of peroxygen in water.

Method for Determining the Concentration of Peroxycarboxylic Acid and Hydrogen Peroxide.

A variety of analytical methods can be used in the present method to analyze the reactants and products including, but not limited to, titration, high performance liquid chromatography (HPLC), gas chromatography (GC), mass spectroscopy (MS), capillary electrophoresis (CE), the HPLC analytical procedure described by U. Karst et al. (*Anal. Chem.,* 69(17):3623-3627 (1997)), and the 2,2'-azino-bis(3-ethylbenzothazoline)-6-sulfonate (ABTS) assay (see U. Pinkernell et al., *The Analyst* 122:567-571 (1997); S. Minning, et al., *Analytica Chimica Acta* 378:293-298 (1999) and WO 2004/058961 A1) as described in U.S. Pat. No. 7,951,566.

Determination of Minimum Biocidal Concentration of Peroxycarboxylic Acids

The method described by J. Gabrielson et al. (*J. Microbiol. Methods* 50: 63-73 (2002)) can be employed for determination of the Minimum Biocidal Concentration (MBC) of peroxycarboxylic acids, or of hydrogen peroxide and enzyme substrates. The assay method is based on XTT reduction inhibition, where XTT (2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to, viable plate counts, direct microscopic counts, dry weight, turbidity measurements, absorbance, and bioluminescence (see, for example Brock, Semour S., *Disinfection, Sterilization, and Preservation,* 5$^{th}$ edition, Lippincott Williams & Wilkins, Philadelphia, Pa., USA; 2001).

Uses of Enzymatically Prepared Peroxycarboxylic Acid Compositions

The enzyme catalyst-generated peroxycarboxylic acid produced according to the present method can be used in a variety of hard surface/inanimate object applications for reduction of concentrations of biological contaminants, such as decontamination of medical instruments (e.g., endoscopes), textiles (such as garments and carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peroxycarboxylic acids may be used in formulations designed to inactivate prions (e.g., certain proteases) to additionally provide biocidal activity (see U.S. Pat. No. 7,550,420 to DiCosimo et al.).

In one aspect, the peroxycarboxylic acid composition is useful as a disinfecting agent for non-autoclavable medical instruments and food packaging equipment. As the peroxycarboxylic acid-containing formulation may be prepared using GRAS (generally recognized as safe) or food-grade components (enzyme, enzyme substrate, hydrogen peroxide, and buffer), the enzyme-generated peroxycarboxylic acid may also be used for decontamination of animal carcasses, meat, fruits and vegetables, or for decontamination of prepared foods. The enzyme-generated peroxycarboxylic acid may be incorporated into a product whose final form is a powder, liquid, gel, film, solid or aerosol. The enzyme-generated peroxycarboxylic acid may be diluted to a concentration that still provides an efficacious decontamination.

The compositions comprising an efficacious concentration of peroxycarboxylic acid can be used to disinfect surfaces and/or objects contaminated (or suspected of being contaminated) with biological contaminants, such as pathogenic microbial contaminants, by contacting the surface or object with the products produced by the present processes. As used herein, "contacting" refers to placing a disinfecting composition comprising an effective concentration of peroxycarboxylic acid in contact with the surface or inanimate object suspected of contamination with a biological contaminant for a period of time sufficient to clean and disinfect. Contacting includes spraying, treating, immersing, flushing, pouring on or in, mixing, combining, painting, coating, applying, affixing to and otherwise communicating a peroxycarboxylic acid solution or composition comprising an efficacious concentration of peroxycarboxylic acid, or a solution or composition that forms an efficacious concentration of peroxycarboxylic acid, with the surface or inanimate object suspected of being contaminated with a concentration of a biological contaminant. The disinfectant compositions may be combined with a cleaning composition to provide both cleaning and disinfection. Alternatively, a cleaning agent (e.g., a surfactant or detergent) may be incorporated into the formulation to provide both cleaning and disinfection in a single composition.

The compositions comprising an efficacious concentration of peroxycarboxylic acid can also contain at least one additional antimicrobial agent, combinations of prion-degrading proteases, a virucide, a sporicide, or a biocide. Combinations of these agents with the peroxycarboxylic acid produced by the claimed processes can provide for increased and/or synergistic effects when used to clean and disinfect surfaces and/or objects contaminated (or suspected of being contaminated) with biological contaminants. Suitable antimicrobial agents include carboxylic esters (e.g., p-hydroxy alkyl benzoates and alkyl cinnamates); sulfonic acids (e.g., dodecylbenzene sulfonic acid); iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite); organic peroxides including benzoyl peroxide, alkyl benzoyl peroxides, ozone, singlet oxygen generators, and mixtures thereof; phenolic derivatives (e.g., o-phenyl phenol, o-benzyl-p-chlorophenol, tert-amyl phenol and $C_1$-$C_6$ alkyl hydroxy benzoates); quaternary ammonium compounds (e.g., alkyldimethylbenzyl ammonium chloride, dialkyldimethyl ammonium chloride and mixtures thereof); and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peroxycarboxylic acids formed by the process can be used to reduce the concentration of viable biological contaminants (such as a microbial population) when applied on and/or at a locus. As used herein, a "locus" comprises part or all of a target surface suitable for disinfecting or bleaching. Target surfaces include all surfaces that can potentially be contaminated with biological contaminants.

Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment (such as endoscopes), clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, wood pulp, paper, vinyl, linoleum, and carpet.

The peroxycarboxylic acids formed by the present process may be used to provide a benefit to an article of clothing or a textile including, but not limited to, disinfecting, sanitizing, bleaching, destaining, and deodorizing. The peroxycarboxylic acids formed by the present process may be used in any number of laundry care products including, but not limited to, textile pre-wash treatments, laundry detergents, laundry detergents or additives, stain removers, bleaching compositions, deodorizing compositions, and rinsing agents, to name a few.

The peroxycarboxylic acids formed by the present process can be used in one or more steps of the wood pulp or paper pulp bleaching/delignification process, particularly where peracetic acid is used (for example, see EP1040222 B1 and U.S. Pat. No. 5,552,018 to Devenyns, J.).

Personal Care Applications

The perhydrolytic enzymes described herein can be used to produce a peracid benefit agent for personal applications such as hair care (bleaching, depilatory), skincare (skin lightening, antimicrobial), and oral care applications (teeth whitening/bleaching or antiseptic), to name a few. The compositions and methods described herein may further comprise one or more dermatologically or cosmetically acceptable components known or otherwise effective for use in hair care, skin care, nail care or other personal care products, provided that the optional components are physically and chemically compatible with the essential components described herein, or do not otherwise unduly impair product stability, aesthetics, or performance. Non-limiting examples of such optional components are disclosed in *International Cosmetic Ingredient Dictionary*, Ninth Edition, 2002, and CTFA Cosmetic Ingredient Handbook, Tenth Edition, 2004.

In one embodiment, the dermatologically/cosmetically acceptable carrier may comprise from about 10 wt % to about 99.9 wt %, alternatively from about 50 wt % to about 95 wt %, and alternatively from about 75 wt % to about 95 wt %, of a dermatologically acceptable carrier. Carriers suitable for use with the composition(s) may include, for example, those used in the formulation of hair sprays, mousses, tonics, gels, skin moisturizers, lotions, and leave-on conditioners. The carrier may comprise water; organic oils; silicones such as volatile silicones, amino or non-amino silicone gums or oils, and mixtures thereof; mineral oils; plant oils such as olive oil, castor oil, rapeseed oil, coconut oil, wheatgerm oil, sweet almond oil, avocado oil, *macadamia* oil, apricot oil, safflower oil, candlenut oil, false flax oil, tamanu oil, lemon oil and mixtures thereof; waxes; and organic compounds such as $C_2$-$C_{10}$ alkanes, acetone, methyl ethyl ketone, volatile organic $C_1$-$C_{12}$ alcohols, esters (with the understanding that the choice of ester(s) may be dependent on whether or not it may act as a carboxylic acid ester substrates for the perhydrolases) of $C_1$-$C_{20}$ acids and of $C_1$-$C_8$ alcohols such as methyl acetate, butyl acetate, ethyl acetate, and isopropyl myristate, dimethoxyethane, diethoxyethane, $C_{10}$-$C_{30}$ fatty alcohols such as lauryl alcohol, cetyl alcohol, stearyl alcohol, and behenyl alcohol; $C_{10}$-$C_{30}$ fatty acids such as lauric acid and stearic acid; $C_{10}$-$C_{30}$ fatty amides such as lauric diethanolamide; $C_{10}$-$C_{30}$ fatty alkyl esters such as $C_{10}$-$C_{30}$ fatty alkyl benzoates; hydroxypropylcellulose; and mixtures thereof. In one embodiment, the carrier comprises water, fatty alcohols, volatile organic alcohols, and mixtures thereof. The composition(s) of the present invention further may comprise from about 0.1% to about 10%, and alternatively from about 0.2% to about 5.0%, of a gelling agent to help provide the desired viscosity to the composition(s). Non-limiting examples of suitable optional gelling agents include crosslinked carboxylic acid polymers; unneutralized crosslinked carboxylic acid polymers; unneutralized modified crosslinked carboxylic acid polymers; crosslinked ethylene/maleic anhydride copolymers; unneutralized crosslinked ethylene/maleic anhydride copolymers (e.g., EMA 81 commercially available from Monsanto); unneutralized crosslinked alkyl ether/acrylate copolymers (e.g., SALCARE™ SC90 commercially available from Allied Colloids); unneutralized crosslinked copolymers of sodium polyacrylate, mineral oil, and PEG-1 trideceth-6 (e.g., SALCARE™ SC91 commercially available from Allied Colloids); unneutralized crosslinked copolymers of methyl vinyl ether and maleic anhydride (e.g., STABILEZE™ QM-PVM/MA copolymer commercially available from International Specialty Products); hydrophobically modified nonionic cellulose polymers; hydrophobically modified ethoxylate urethane polymers (e.g., UCARE™Polyphobe Series of alkali swellable polymers commercially available from Union Carbide); and combinations thereof. In this context, the term "unneutralized" means that the optional polymer and copolymer gelling agent materials contain unneutralized acid monomers. Preferred gelling agents include water-soluble unneutralized crosslinked ethylene/maleic anhydride copolymers, water-soluble unneutralized crosslinked carboxylic acid polymers, water-soluble hydrophobically modified nonionic cellulose polymers and surfactant/fatty alcohol gel networks such as those suitable for use in hair conditioning products.

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, bacterial host strains include *Escherichia, Bacillus*, and *Pseudomonas*. In a preferred embodiment, the bacterial host cell is *Bacillus subtilis* or *Escherichia coli*.

Industrial Production

A variety of culture methodologies may be applied to produce the perhydrolase catalyst. Large-scale production of a specific gene product over expressed from a recombinant microbial host may be produced by batch, fed-batch or continuous culture methodologies. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227 (1992).

In one embodiment, commercial production of the desired perhydrolase catalyst is accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Recovery of the desired perhydrolase catalysts from a batch or fed-batch fermentation, or continuous culture may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein produced during the heat-treatment step by membrane filtration or centrifugation, and the resulting partially-purified enzyme catalyst solution concentrated by additional membrane filtration, then optionally mixed with an appropriate excipient (for example, maltodextrin, trehalose, sucrose, lactose, sorbitol, mannitol, phosphate buffer, citrate buffer, or mixtures thereof) and spray-dried to produce a solid powder comprising the desired enzyme catalyst. Alternatively, the resulting partially-purified enzyme catalyst solution prepared as described above may be optionally concentrated by additional membrane filtration, and the partially-purified enzyme catalyst solution or resulting enzyme concentrate is then optionally mixed with one or more stabilizing agents (e.g., glycerol, sorbitol, propylene glycol, 1,3-propanediol, polyols, polymeric polyols, polyvinylalcohol or mixtures thereof), one or more salts (e.g., sodium chloride, sodium sulfate, potassium chloride, potassium sulfate, or mixtures thereof), and one or more biocides, and maintained as an aqueous solution until used.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

GENERAL METHODS

The following examples are provided to demonstrate different embodiments. It should be appreciated by those of skill in the art that the techniques disclosed in the examples which follow represent techniques discovered by the inventor to function well in the practice of the methods disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma-Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "μL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "μg" means microgram(s), "ng" means nanogram(s), "g" means gravity, "HPLC" means high performance liquid chromatography, "dd H$_2$O" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, "EDTA" means ethylenediaminetetraacetic acid, "IPTG" means isopropyl-β-D-thio-galactoside, "BCA" means bicinchoninic acid, and "ABTS" means 2,2'-azino-bis(3-ethylbenzothiazoline-6-sulfonate).

Example 1

Cloning and Production of CE-7 Acetyl Xylan Esterase from *Actinosynnema mirum* in *E. coli*

The gene encoding the acetyl xylan esterase enzyme from *Actinosynnema mirum* as reported in GENBANK® (Accession No. ACU35776.1; GI:255920265) was synthesized using codons optimized for expression in *E. coli* (DNA 2.0, Menlo Park, Calif.). The nucleic acid product (SEQ ID NO: 3) was subcloned into PJEXPRESS404® (DNA 2.0, Menlo Park, Calif.) to generate the plasmid identified as pMP91. The plasmid pMP91 was used to transform *E. coli* KLP18 (described in U.S. Pat. No. 7,723,083) to generate the strain identified as KLP18/pMP91. KLP18/pMP91 was grown in LB media at 37° C. with shaking up to $OD_{600\ nm}$=0.4-0.5, at which time IPTG was added to a final concentration of 1 mM, and incubation continued for 2-3 h. Cells were harvested by centrifugation at 5,000×g for 15 minutes then resuspended (20% w/v) in 50 mM potassium phosphate buffer pH 7.0 supplemented with 1.0 mM dithiothreitol. Resuspended cells were passed through a French pressure cell twice. Lysed cells were centrifuged for 30 minutes at 12,000×g and the protein concentration in the extract supernatant was determined using a BCA assay kit (Sigma-Aldrich, St. Louis, Mo.). SDS-PAGE was used to confirm expression of the CE-7 enzyme (SEQ ID NO: 4), and analysis of the gels using ImageJ, a public domain Java image processing program, indicated that perhydrolase constituted 11% of total soluble protein.

Example 2

Cloning and Production of CE-7 Acetyl Xylan Esterase from *Propionibacterium acnes* in *E. coli*

The gene encoding the acetyl xylan esterase enzyme from *Propionibacterium acnes* as reported in GENBANK® (Accession no. AEE71478.1; GI:332674662) was synthesized using codons optimized for expression in *E. coli* (DNA 2.0, Menlo Park, Calif.). The nucleic acid product (SEQ ID NO: 5) was subcloned into PJEXPRESS404® (DNA 2.0, Menlo Park, Calif.) to generate the plasmid identified as pMP92. The plasmid pMP92 was used to transform *E. coli* KLP18 (described in U.S. Pat. No. 7,723,083) to generate the strain identified as KLP18/pMP92. KLP18/pMP92 was grown in LB media at 37° C. with shaking up to $OD_{600\ nm}$=0.4-0.5, at which time IPTG was added to a final concentration of 1 mM, and incubation continued for 2-3 h. Cells were harvested by centrifugation at 5,000×g for 15 minutes then resuspended (20% w/v) in 50 mM potassium phosphate buffer pH 7.0 supplemented with 1.0 mM dithiothreitol. Resuspended cells were passed through a French pressure cell twice. Lysed cells were centrifuged for 30 minutes at 12,000×g and the total soluble protein concentration in the extract supernatant was determined using a BCA assay kit (Sigma-Aldrich, St. Louis, Mo.). SDS-PAGE was used to confirm expression of the CE-7 enzyme (SEQ ID NO: 6), and analysis of the gels using ImageJ, a public domain Java image processing program, indicated that perhydrolase constituted 13% of total soluble protein.

Example 3

Cloning and Production of CE-7 Acetyl Xylan Esterase from *Streptococcus equi* in *E. coli*

The gene encoding the acetyl xylan esterase enzyme from *Streptococcus equi* as reported in GENBANK® (Accession no. CAX00506.1: GI: 225702544) was synthesized using codons optimized for expression in *E. coli* (DNA 2.0, Menlo Park, Calif.). The nucleic acid product (SEQ ID NO: 7) was subcloned into PJEXPRESS404® (DNA 2.0, Menlo Park, Calif.) to generate the plasmid identified as pMP93. The plasmid pMP93 was used to transform *E. coli* KLP18 (described in U.S. Pat. No. 7,723,083) to generate the strain identified as KLP18/pMP93. KLP18/pMP93 was grown in LB media at 37° C. with shaking up to $OD_{600\ nm}$=0.4-0.5, at which time IPTG was added to a final concentration of 1 mM, and incubation continued for 2-3 h. Cells were harvested by centrifugation at 5,000×g for 15 minutes then resuspended (20% w/v) in 50 mM potassium phosphate buffer pH 7.0 supplemented with 1.0 mM dithiothreitol. Resuspended cells were passed through a French pressure cell twice. Lysed cells were centrifuged for 30 minutes at 12,000×g and the total soluble protein concentration in the extract supernatant was determined using a BCA assay kit (Sigma-Aldrich, St. Louis, Mo.). SDS-PAGE was used to confirm expression of the CE-7 enzyme (SEQ ID NO: 8), and analysis of the gels using ImageJ, a public domain Java image processing program, indicated that perhydrolase constituted 26% of total soluble protein.

Example 4

Cloning and Production of CE-7 Acetyl Xylan Esterase from *Stackebrandtia nassauensis* in *E. coli*

The gene encoding the acetyl xylan esterase enzyme from *Stackebrandtia nassauensis* as reported in GENBANK® (Accession No. ADD42786.1: GI:290569821) was synthesized using codons optimized for expression in *E. coli* (DNA 2.0, Menlo Park, Calif.). The nucleic acid product (SEQ ID NO: 9) was subcloned into PJEXPRESS404® (DNA 2.0, Menlo Park, Calif.) to generate the plasmid identified as pMP94. The plasmid pMP91 was used to transform *E. coli* KLP18 (described in U.S. Pat. No. 7,723,083) to generate the strain identified as KLP18/pMP94. KLP18/pMP94 was grown in LB media at 37° C. with shaking up to $OD_{600\ nm}$=0.4-0.5, at which time IPTG was added to a final concentration of 1 mM, and incubation continued for 2-3 h. Cells were harvested by centrifugation at 5,000×g for 15 minutes then resuspended (20% w/v) in 50 mM potassium phosphate buffer pH 7.0 supplemented with 1.0 mM dithiothreitol. Resuspended cells were passed through a French pressure cell twice. Lysed cells were centrifuged for 30 minutes at 12,000×g and the total soluble protein concentration in the extract supernatant was determined using a BCA assay kit (Sigma-Aldrich, St. Louis, Mo.). SDS-PAGE was used to confirm expression of the CE-7 enzyme (SEQ ID NO: 10), and analysis of the gels using ImageJ, a public domain Java image processing program, indicated that perhydrolase constituted 33% of total soluble protein.

Example 5

Cloning and Production of CE-7 Acetyl Xylan Esterase from *Streptococcus agalactiae* in *E. coli*

The gene encoding the acetyl xylan esterase enzyme from *Streptococcus agalactiae* as reported in GENBANK® (Accession No. AAM98949.1; GI:22533045) was synthesized using codons optimized for expression in *E. coli* (DNA 2.0, Menlo Park, Calif.). The nucleic acid product (SEQ ID NO: 11) was subcloned into PJEXPRESS404® (DNA 2.0, Menlo Park, Calif.) to generate the plasmid identified as pMP95. The plasmid pMP95 was used to transform *E. coli* KLP18 (described in U.S. Pat. No. 7,723,083) to generate the strain identified as KLP18/pMP95. KLP18/pMP95 was grown in LB media at 37° C. with shaking up to $OD_{600\,nm}$=0.4-0.5, at which time IPTG was added to a final concentration of 1 mM, and incubation continued for 2-3 h. Cells were harvested by centrifugation at 5,000×g for 15 minutes then resuspended (20% w/v) in 50 mM potassium phosphate buffer pH 7.0 supplemented with 1.0 mM dithiothreitol. Resuspended cells were passed through a French pressure cell twice. Lysed cells were centrifuged for 30 minutes at 12,000×g and the total soluble protein concentration in the extract supernatant was determined using a BCA assay kit (Sigma-Aldrich, St. Louis, Mo.). SDS-PAGE was used to confirm expression of the CE-7 enzyme (SEQ ID NO: 12), and analysis of the gels using ImageJ, a public domain Java image processing program, indicated that perhydrolase constituted 7.3% of total soluble protein.

Example 6

Perhydrolase Activity Assays

Perhydrolase activity in extract supernatant was determined by reactions containing 22.5 mM triacetin, 22.5 mM hydrogen peroxide and 6.25 µg extract supernatant total soluble protein/mL. Incubation was for 10 minutes at ambient temperature (22-24° C.). Reactions were stopped by adding an equal volume of 1.25 M phosphoric acid containing 100 mM ortho-phenylenediamine. After 30 minutes, the absorbance at 458 nm was measured (Table 1). Additional perhydrolase activity measurements were made in reactions containing 10 mM triacetin and 10 mM hydrogen peroxide or 50 mM triacetin and 50 mM hydrogen peroxide (Table 1). CE-7 acetyl xylan esterase from *T. maritima* was also produced in *E. coli* KLP18 (described in US Patent Application Publication 2008-0176299) and used as a positive control for the perhydrolase assay. *E. coli* KLP18 extract not containing a CE-7 enzyme was used a negative control.

TABLE 1

| | | | | OD 458 nm | | |
|---|---|---|---|---|---|---|
| CE-7 esterase source | ref | SEQ ID NO: | triacetin $H_2O_2$ | 10 mM 10 mM | 22.5 mM 22.5 mM | 50 mM 50 mM |
| A. mirum | Ami | 4 | | 0.6 | 2.3 | 2.9 |
| P. acnes | Pac | 6 | | 0.4 | 1.2 | 2.5 |
| S. equi | Seq | 8 | | 0.3 | 1.9 | 2.0 |

TABLE 1-continued

| | | | | OD 458 nm | | |
|---|---|---|---|---|---|---|
| CE-7 esterase source | ref | SEQ ID NO: | triacetin $H_2O_2$ | 10 mM 10 mM | 22.5 mM 22.5 mM | 50 mM 50 mM |
| S. nassauensis | Sna | 10 | | 0.1 | 0.2 | 0.8 |
| S. agalactiae | Sag | 12 | | 0.0 | 0.1 | 0.3 |
| T. maritima | Tma | 2 | | 0.2 | 1.0 | 2.5 |
| none (control) | | | | 0.0 | 0.0 | 0.0 |

Example 7

Production of Peracetic Acid from Triacetin and Hydrogen Peroxide by CE-7 Esterases Reactions (10 mL total volume) were run at 25° C. in potassium phosphate buffer (50 mM, pH 7.0) containing triacetin (10 mM), hydrogen peroxide (20 mM) and 5.0 µg/mL of extract supernatant total soluble protein containing the CE-7 esterase from *Actinosynnema mirum* (SEQ ID NO: 4), *Propionibacterium acnes* (SEQ ID NO: 6), *Streptococcus equi* (SEQ ID NO: 8), *Stackebrandtia nassauensis* (SEQ ID NO: 10) or *Streptococcus agalactiae* (SEQ ID NO: 12), prepared as described in Examples 1-5. Reactions were stirred for only the first 45 seconds of reaction to initially mix the reactants and enzyme. A comparative control reaction was run under identical conditions to that described immediately above using 5.0 µg/mL of extract total soluble protein isolated from *E. coli* KLP18 (used to express the CE-7 esterases), where the extract supernatant was prepared according to the procedure of Example 1. A second comparative control reaction was also run under identical conditions to that described immediately above using no added extract supernatant total soluble protein, where peracetic acid produced in the absence of added esterase was the result of chemical perhydrolysis of triacetin by hydrogen peroxide under the specified reaction conditions. The CE-7 acetyl xylan esterase from *T. maritima* (SEQ ID NO: 2) was also produced in *E. coli* KLP18 (described in US Patent Application Publication 2008-0176299) and used as a positive control in a comparative reaction (11% of total soluble protein in cell extract supernatant).

Analysis of reaction samples for the production of peracetic acid followed the method described in Pinkernell et. al. (*Analyst*, 122:567 (1997)) using colorimetric detection of ABTS oxidation by peracetic acid. A 50 µL reaction sample was added to 950 µL of 5 mM $H_3PO_4$ to stop the enzymatic reaction (final pH between pH 2-3), and 50 µL of the resulting solution was added to a 96-well microtiter plate well containing 200 µL of an aqueous solution containing 0.25 M acetic acid, 0.125 g/L ABTS and 5.0 mg/L of KI. The solution was allowed to develop for 5 min, then the absorbance of the solution was measured at 405 nm using a microplate reader. The peracetic acid concentration in each sample was calculated from a standard curve developed simultaneously using a peracetic acid reagent solution (Table 2).

TABLE 2

CE-7 perhydrolase-catalyzed production of peracetic acid (PAA) from triacetin and hydrogen peroxide in potassium phosphate buffer (50 mM, pH 7.0) at 25° C.

| CE-7 esterase source | SEQ ID NO | triacetin (mM) | $H_2O_2$ (mM) | total soluble protein (µg/mL) | PAA at 2 min (ppm) | PAA at 5 min (ppm) | PAA at 10 min (ppm) | PAA at 20 min (ppm) | PAA at 30 min (ppm) |
|---|---|---|---|---|---|---|---|---|---|
| control - no enzyme | | 10 | 20 | 0 | 4.1 | 4.3 | 3.1 | 4.0 | 4.6 |
| control - *E. coli* KLP18 | | 10 | 20 | 5.0 | 3.9 | 4.0 | 4.1 | 4.0 | 4.8 |
| A. mirum | 4 | 10 | 20 | 5.0 | 8.8 | 17 | 30 | 50 | 68 |
| P. acnes | 6 | 10 | 20 | 5.0 | 6.4 | 12 | 18 | 28 | 36 |

TABLE 2-continued

CE-7 perhydrolase-catalyzed production of peracetic acid (PAA) from triacetin and hydrogen peroxide in potassium phosphate buffer (50 mM, pH 7.0) at 25° C.

| CE-7 esterase source | SEQ ID NO | triacetin (mM) | $H_2O_2$ (mM) | total soluble protein (μg/mL) | PAA at 2 min (ppm) | PAA at 5 min (ppm) | PAA at 10 min (ppm) | PAA at 20 min (ppm) | PAA at 30 min (ppm) |
|---|---|---|---|---|---|---|---|---|---|
| S. equi | 8 | 10 | 20 | 5.0 | 18 | 33 | 47 | 53 | 52 |
| S. nassauensis | 10 | 10 | 20 | 5.0 | 4.3 | 6.0 | 7.8 | 11 | 15 |
| S. agalactiae | 12 | 10 | 20 | 5.0 | 4.3 | 4.5 | 5.1 | 6.6 | 7.4 |
| T. maritima | 2 | 10 | 20 | 5.0 | 5.6 | 11 | 16 | 28 | 43 |

Example 8

Production of Peracetic Acid from Propylene Glycol Diacetate and Hydrogen Peroxide by CE-7 Esterases Reactions (10 mL total volume) were run at 25° C. in potassium phosphate buffer (50 mM, pH 7.0) containing propylene glycol diacetate (10 mM), hydrogen peroxide (20 mM) and 5.0 μg/mL of extract supernatant total soluble protein containing the CE-7 esterase from *Actinosynnema mirum* (SEQ ID NO: 4), *Propionibacterium acnes* (SEQ ID NO: 6), *Streptococcus equi* (SEQ ID NO: 8), or *Stackebrandtia nassauensis* (SEQ ID NO: 10) prepared as described in Examples 1-4. Reactions were stirred for only the first 45 seconds of reaction to initially mix the reactants and enzyme. A comparative control reaction was run under identical conditions to that described immediately above using 5.0 μg/mL of extract total soluble protein isolated from *E. coli* KLP18 (used to express the CE-7 esterases), where the extract supernatant was prepared according to the procedure of Example 1. A second comparative control reaction was also run under identical conditions to that described immediately above using no added extract supernatant total soluble protein, where peracetic acid produced in the absence of added esterase was the result of chemical perhydrolysis of propylene glycol diacetate by hydrogen peroxide under the specified reaction conditions. The CE-7 acetyl xylan esterase from *T. maritima* (SEQ ID NO: 2) was also produced in *E. coli* KLP18 (described in US Patent Application Publication 2008-0176299) and used as a positive control in a comparative reaction (11% of total soluble protein in cell extract supernatant). Analysis of reaction samples for the production of peracetic acid followed the method described in Example 7 (Table 3).

Example 9

Production of Peracetic Acid from α-D-Glucose Pentaacetate and Hydrogen Peroxide by CE-7 Esterases Reactions (10 mL total volume) were run at 25° C. in potassium phosphate buffer (50 mM, pH 7.0) containing α-D-glucose pentaacetate (10 mM), hydrogen peroxide (20 mM) and 5.0 μg/mL of extract supernatant total soluble protein containing the CE-7 esterase from *Actinosynnema mirum* (SEQ ID NO: 4), *Streptococcus equi* (SEQ ID NO: 8), or *Streptococcus agalactiae* (SEQ ID NO: 12) prepared as described in Examples 1, 3 and 5. Reactions were stirred for only the first 45 seconds of reaction to initially mix the reactants and enzyme. A comparative control reaction was run under identical conditions to that described immediately above using 5.0 μg/mL of extract total soluble protein isolated from *E. coli* KLP18 (used to express the CE-7 esterases), where the extract supernatant was prepared according to the procedure of Example 1. A second comparative control reaction was also run under identical conditions to that described immediately above using no added extract supernatant total soluble protein, where peracetic acid produced in the absence of added esterase was the result of chemical perhydrolysis of α-D-glucose pentaacetate by hydrogen peroxide under the specified reaction conditions. The CE-7 acetyl xylan esterase from *T. maritima* (SEQ ID NO: 2) was also produced in *E. coli* KLP18 (described in US Patent Application Publication 2008-0176299) and used as a positive control in a comparative reaction (11% of total soluble protein in cell extract supernatant). Analysis of reaction samples for the production of peracetic acid followed the method described in Example 7 (Table 4).

TABLE 3

CE-7 perhydrolase-catalyzed production of peracetic acid (PAA) from propylene glycol diacetate and hydrogen peroxide in potassium phosphate buffer (50 mM, pH 7.0) at 25° C.

| CE-7 esterase source | SEQ ID NO | propylene glycol diacetate (mM) | $H_2O_2$ (mM) | total soluble protein (μg/mL) | PAA at 2 min (ppm) | PAA at 5 min (ppm) | PAA at 10 min (ppm) | PAA at 20 min (ppm) | PAA at 30 min (ppm) |
|---|---|---|---|---|---|---|---|---|---|
| control - no enzyme | | 10 | 20 | 0 | 5.4 | 5.0 | 5.0 | 5.2 | 5.1 |
| control - *E. coli* KLP18 | | 10 | 20 | 5.0 | 5.4 | 5.1 | 5.2 | 5.1 | 5.2 |
| A. mirum | 4 | 10 | 20 | 5.0 | 8.0 | 13 | 22 | 35 | 47 |
| P. acnes | 6 | 10 | 20 | 5.0 | 6.1 | 6.9 | 8.6 | 13 | 12 |
| S. equi | 8 | 10 | 20 | 5.0 | 6.6 | 11 | 11 | 12 | 12 |
| S. nassauensis | 10 | 10 | 20 | 5.0 | 4.6 | 4.8 | 8.2 | 6.4 | 7.6 |
| T. maritima | 2 | 10 | 20 | 5.0 | 5.7 | 6.8 | 8.3 | 12 | 15 |

TABLE 4

CE-7 perhydrolase-catalyzed production of peracetic acid (PAA) from α-D-glucose pentaacetate and hydrogen peroxide in potassium phosphate buffer (50 mM, pH 7.0) at 25° C.

| CE-7 esterase source | SEQ ID NO | α-D-glucose pentaacetate (mM) | $H_2O_2$ (mM) | total soluble protein (μg/mL) | PAA at 2 min (ppm) | PAA at 5 min (ppm) | PAA at 10 min (ppm) | PAA at 20 min (ppm) | PAA at 30 min (ppm) |
|---|---|---|---|---|---|---|---|---|---|
| control - no enzyme | | 10 | 20 | 0 | 6.7 | 18 | 41 | 93 | 136 |
| control - E. coli KLP18 | | 10 | 20 | 5.0 | 8.7 | 20 | 46 | 94 | 137 |
| A. mirum | 4 | 10 | 20 | 5.0 | 20 | 34 | 68 | 130 | 179 |
| S. equi | 8 | 10 | 20 | 5.0 | 11 | 23 | 46 | 93 | 141 |
| S. agalactiae | 12 | 10 | 20 | 5.0 | 16 | 29 | 51 | 99 | 148 |
| T. maritima | 2 | 10 | 20 | 5.0 | 11 | 24 | 47 | 99 | 144 |

Example 10

Production of Peracetic Acid from D-Sorbitol Hexaacetate and Hydrogen Peroxide by CE-7 Esterases Reactions (10 mL total volume) were run at 25° C. in potassium phosphate buffer (50 mM, pH 7.0) containing D-sorbitol hexaacetate (10 mM), hydrogen peroxide (20 mM) and 5.0 μg/mL of extract supernatant total soluble protein containing the CE-7 esterase from *Actinosynnema mirum* (SEQ ID NO: 4), or *Streptococcus equi* (SEQ ID NO: 8) prepared as described in Examples 1 and 3. Reactions were stirred for only the first 45 seconds of reaction to initially mix the reactants and enzyme. A comparative control reaction was run under identical conditions to that described immediately above using 5.0 μg/mL of extract total soluble protein isolated from *E. coli* KLP18 (used to express the CE-7 esterases), where the extract supernatant was prepared according to the procedure of Example 1. A second comparative control reaction was also run under identical conditions to that described immediately above using no added extract supernatant total soluble protein, where peracetic acid produced in the absence of added esterase was the result of chemical perhydrolysis of D-sorbitol hexaacetate by hydrogen peroxide under the specified reaction conditions. The CE-7 acetyl xylan esterase from *T. maritima* (SEQ ID NO: 2) was also produced in *E. coli* KLP18 (described in US Patent Application Publication 2008-0176299) and used as a positive control in a comparative reaction (11% of total soluble protein in cell extract supernatant). Analysis of reaction samples for the production of peracetic acid followed the method described in Example 7 (Table 5).

Example 11

Production of Peracetic Acid from Tri-O-Acetyl-D-Glucal and Hydrogen Peroxide by CE-7 Esterases Reactions (50 mL total volume) were run at 25° C. in potassium phosphate buffer (10 mM, pH 7.0) containing tri-O-acetyl-D-glucal (2 mM), hydrogen peroxide (10 mM) and 5.0 μg/mL of extract supernatant total soluble protein containing the CE-7 esterase from *Actinosynnema mirum* (SEQ ID NO: 4) or *Streptococcus equi* (SEQ ID NO: 8) prepared as described in Examples 1 and 3. Reactions were stirred for only the first 45 seconds of reaction to initially mix the reactants and enzyme. A comparative control reaction was run under identical conditions to that described immediately above using 5.0 μg/mL of extract total soluble protein isolated from *E. coli* KLP18 (used to express the CE-7 esterases), where the extract supernatant was prepared according to the procedure of Example 1. A second comparative control reaction was also run under identical conditions to that described immediately above using no added extract supernatant total soluble protein, where peracetic acid produced in the absence of added esterase was the result of chemical perhydrolysis of tri-O-acetyl-D-glucal by hydrogen peroxide under the specified reaction conditions. The CE-7 acetyl xylan esterase from *T. maritima* (SEQ ID NO: 2) was also produced in *E. coli* KLP18 (described in US Patent Application Publication 2008-0176299) and used as a positive control in a comparative reaction (11% of total soluble protein in cell extract supernatant). Analysis of reaction samples for the production of peracetic acid followed the method described in Example 7 (Table 6).

TABLE 5

CE-7 perhydrolase-catalyzed production of peracetic acid (PAA) from D-sorbitol hexaacetate and hydrogen peroxide in potassium phosphate buffer (50 mM, pH 7.0) at 25° C.

| CE-7 esterase source | SEQ ID NO | D-sorbitol hexaacetate (mM) | $H_2O_2$ (mM) | total soluble protein (μg/mL) | PAA at 2 min (ppm) | PAA at 5 min (ppm) | PAA at 10 min (ppm) | PAA at 20 min (ppm) | PAA at 30 min (ppm) |
|---|---|---|---|---|---|---|---|---|---|
| control - no enzyme | | 10 | 20 | 0 | 3.6 | 3.9 | 4.4 | 4.2 | 4.5 |
| control - E. coli KLP18 | | 10 | 20 | 5.0 | 3.8 | 4.2 | 4.1 | 4.1 | 4.7 |
| A. mirum | 4 | 10 | 20 | 5.0 | 5.6 | 9.0 | 15 | 25 | 34 |
| S. equi | 8 | 10 | 20 | 5.0 | 4.8 | 5.9 | 7.7 | 9.1 | 9.8 |
| T. maritima | 2 | 10 | 20 | 5.0 | 5.0 | 6.0 | 11 | 15 | 21 |

TABLE 6

CE-7 perhydrolase-catalyzed production of peracetic acid (PAA) from tri-O-acetyl-D-glucal and hydrogen peroxide in potassium phosphate buffer (10 mM, pH 7.0) at 25° C.

| CE-7 esterase source | SEQ ID NO: | tri-O-acetyl-D-glucal (mM) | $H_2O_2$ (mM) | total soluble protein (μg/mL) | PAA at 5 min (ppm) | PAA at 20 min (ppm) |
|---|---|---|---|---|---|---|
| control - no enzyme |  | 2 | 10 | 0 | 2.6 | 2.2 |
| control - E. coli KLP18 |  | 2 | 10 | 5.0 | 2.5 | 1.5 |
| A. mirum | 4 | 2 | 10 | 5.0 | 6.7 | 18 |
| S. equi | 8 | 2 | 10 | 5.0 | 5.8 | 6.4 |
| T. maritima | 2 | 2 | 10 | 5.0 | 4.9 | 13 |

Example 12

Production of Peracetic Acid from 4-(Acetyloxy)-Benzoic Acid and Hydrogen Peroxide by CE-7 Esterases Reactions (10 mL total volume) were run at 20° C. in potassium phosphate buffer (50 mM, pH 7.0) containing 4-(acetyloxy)-benzoic acid (CAS 2345-34-8; 25 mM), hydrogen peroxide (20 mM) and 5.0 μg/mL of extract supernatant total soluble protein containing the CE-7 esterase from *Actinosynnema mirum* (SEQ ID NO: 4), *Propionibacterium acnes* (SEQ ID NO: 6), *Streptococcus equi* (SEQ ID NO: 8), or *Stackebrandtia nassauensis* (SEQ ID NO: 10) prepared as described in Examples 1-4. Reactions were stirred for only the first 45 seconds of reaction to initially mix the reactants and enzyme. A comparative control reaction was run under identical conditions to that described immediately above using 5.0 μg/mL of heat-treated extract total soluble protein isolated from *E. coli* KLP18 (used to express the CE-7 esterases), where the extract supernatant was prepared according to the procedure of Example 1. A second comparative control reaction was also run under identical conditions to that described immediately above using no added extract supernatant total soluble protein, where peracetic acid produced in the absence of added esterase was the result of chemical perhydrolysis of 4-(acetyloxy)-benzoic acid by hydrogen peroxide under the specified reaction conditions. The CE-7 acetyl xylan esterase from *T. maritima* (SEQ ID NO: 2) was also produced in *E. coli* KLP18 (described in US Patent Application Publication 2008-0176299) and used as a positive control in a comparative reaction (11% of total soluble protein in cell extract supernatant). Analysis of reaction samples for the production of peracetic acid followed the method described in Example 7 (Table 7).

Example 13

Cloning and Production of an *Actinosynnema mirum* Acetyl Xylan Esterase Variant A gene encoding a variant of the acetyl xylan esterase enzyme from *A. mirum* as reported in GENBANK® (Accession No. ACU35776.1: GI: 255920265) was synthesized using codons optimized for expression in *E. coli* (DNA 2.0, Menlo Park, Calif.). The nucleic acid product (SEQ ID NO: 13) was subcloned into PJEXPRESS404® (DNA 2.0, Menlo Park, Calif.) to generate the plasmid identified as pMP91a. The encoded variant protein is called Ami_C276S (SEQ ID NO: 14). The plasmid pMP91a was used to transform *E. coli* KLP18 (described in U.S. Pat. No. 7,723,083) to generate the strain identified as KLP18/pMP91a. KLP18/pMP91a was grown in LB media at 37° C. with shaking up to $OD_{600\ nm}=0.4$-$0.5$, at which time IPTG was added to a final concentration of 1 mM, and incubation continued for 2-3 h. Cells were harvested by centrifugation at 5,000×g for 15 minutes then resuspended (20% w/v) in 50 mM potassium phosphate buffer pH 7.0 supplemented with 1.0 mM dithiothreitol. Resuspended cells were passed through a French pressure cell twice. Lysed cells were centrifuged for 30 minutes at 12,000×g and the protein concentration in the supernatant was determined using a BCA assay kit (Sigma-Aldrich, St. Louis, Mo.). SDS-PAGE was used to confirm expression of the enzyme and densitometry (ImageJ software, National Institutes of Health, Bethesda, Md.) was used to calculate the enzyme protein as approximately 16-18% of the total protein.

Example 14

Cloning and Production of an *Actinosynnema mirum* Acetyl Xylan Esterase Variant

TABLE 7

CE-7 perhydrolase-catalyzed production of peracetic acid (PAA) from 4-(acetyloxy)-benzoic acid and hydrogen peroxide in potassium phosphate buffer (50 mM, pH 7.0) at 20° C.

| CE-7 esterase source | SEQ ID NO | 4-(acetyloxy)-benzoic acid (mM) | $H_2O_2$ (mM) | total soluble protein (μg/mL) | PAA at 5 min (ppm) | PAA at 20 min (ppm) |
|---|---|---|---|---|---|---|
| control - no enzyme |  | 25 | 20 | 0 | 28 | 74 |
| control - E. coli KLP18 |  | 25 | 20 | 5.0 | 21 | 73 |
| A. mirum | 4 | 25 | 20 | 5.0 | 36 | 85 |
| P. acnes | 6 | 25 | 20 | 5.0 | 31 | 90 |
| S. equi | 8 | 25 | 20 | 5.0 | 31 | 98 |
| S. nassauensis | 10 | 25 | 20 | 5.0 | 29 | 80 |
| T. maritima | 2 | 25 | 20 | 5.0 | 21 | 71 |

A gene encoding a variant of the acetyl xylan esterase enzyme from *A. mirum* as reported in GENBANK® (Accession No. ACU35776.1: GI: 255920265) was synthesized using codons optimized for expression in *E. coli* (DNA 2.0, Menlo Park, Calif.). The nucleic acid product (SEQ ID NO: 15) was subcloned into PJEXPRESS404® (DNA 2.0, Menlo Park, Calif.) to generate the plasmid identified as pMP91b. The encoded variant protein is called Ami_C276T (SEQ ID NO: 16). The plasmid pMP91b was used to transform *E. coli* KLP18 (described in U.S. Pat. No. 7,723,083) to generate the strain identified as KLP18/pMP91b. KLP18/pMP91b was grown in LB media at 37° C. with shaking up to $OD_{600\,nm}$=0.4-0.5, at which time IPTG was added to a final concentration of 1 mM, and incubation continued for 2-3 h. Cells were harvested by centrifugation at 5,000×g for 15 minutes then resuspended (20% w/v) in 50 mM potassium phosphate buffer pH 7.0 supplemented with 1.0 mM dithiothreitol. Resuspended cells were passed through a French pressure cell twice. Lysed cells were centrifuged for 30 minutes at 12,000×g and the protein concentration in the supernatant was determined using a BCA assay kit (Sigma-Aldrich, St. Louis, Mo.). SDS-PAGE was used to confirm expression of the enzyme and densitometry (ImageJ software, National Institutes of Health, Bethesda, Md.) was used to calculate the enzyme protein as approximately 16-18% of the total protein.

Example 15

Perhydrolase Activity Assays

Perhydrolase activity in extracts was determined by reactions containing 22.5 mM triacetin, 22.5 mM hydrogen peroxide and 1.5 μg total protein/mL. Incubation was for 10 minutes at ambient temperature (22-24° C.). Reactions were stopped by adding an equal volume of 1.25 M phosphoric acid containing 100 mM ortho-phenylenediamine. After 30 minutes, the absorbance at 458 nm was measured (Table 8). *E. coli* KLP18 extract not containing an acetyl xylan esterase enzyme was used a negative control.

TABLE 8

| Enzyme ID. | SEQ ID NO: | OD 458 nm |
|---|---|---|
| Ami_wt | 4 | 0.21 |
| Ami_C276S | 14 | 2.3 |

TABLE 8-continued

| Enzyme ID. | SEQ ID NO: | OD 458 nm |
|---|---|---|
| Ami_C276T | 16 | 1.5 |
| Control - no enzyme | | 0 |

Example 16

Production of Peracetic Acid from Triacetin and Hydrogen Peroxide by CE-7 Esterase Variants Reactions (10 mL total volume) were run at 25° C. in potassium phosphate buffer (20 mM, pH 7.0) containing triacetin (0.75 mM), hydrogen peroxide (1.4 mM) and either 1.0 μg/mL or 2.0 μg/mL of CE-7 esterase from wild-type *Actinosynnema mirum* (SEQ ID NO: 4, prepared as described in Example 1), *Actinosynnema mirum* C276S variant (SEQ ID NO: 14, prepared as described in Example 13), *Actinosynnema mirum* C276T variant (SEQ ID NO: 16, prepared as described in Example 14), *T. maritima* C277S (SEQ ID NO: 17, produced in *E. coli* KLP18 as described in U.S. Pat. No. 8,062,875), and *T. maritima* C277T (SEQ ID NO:18, produced in *E. coli* KLP18 as described in U.S. Pat. No. 8,062,875). Analysis of cell extracts containing CE-7 esterase by SDS-PAGE gels in combination with analysis of the gels using ImageJ, a public domain Java image processing program, was used to calculate the concentration of CE-7 esterase in cell extracts as a percentage of total soluble protein. Reactions were stirred for only the first 45 seconds of reaction to initially mix the reactants and enzyme. A comparative control reaction was run under identical conditions to that described immediately above using no added CE-7 esterase, where peracetic acid produced in the absence of added esterase was the result of chemical perhydrolysis of triacetin by hydrogen peroxide under the specified reaction conditions. Analysis of reaction samples for the production of peracetic acid followed the method described in Example 7 (Table 9).

TABLE 9

CE-7 perhydrolase variant-catalyzed production of peracetic acid (PAA) from triacetin and hydrogen peroxide in potassium phosphate buffer (20 mM, pH 7.0) at 25° C.

| CE-7 esterase source | SEQ ID NO | triacetin (mM) | $H_2O_2$ (mM) | CE-7 esterase variant (μg/mL) | PAA at 2 min (ppm) | PAA at 5 min (ppm) | PAA at 10 min (ppm) | PAA at 20 min (ppm) | PAA at 30 min (ppm) |
|---|---|---|---|---|---|---|---|---|---|
| control - no enzyme | | 0.75 | 1.4 | 0 | 0.5 | 0.4 | 0.4 | 0.4 | 0.3 |
| *A. mirum* wild-type | 4 | 0.75 | 1.4 | 1.0 | 0.6 | 1.4 | 2.1 | 1.2 | 0.6 |
| *A. mirum* C276S | 14 | 0.75 | 1.4 | 1.0 | 3.1 | 5.4 | 6.8 | 4.9 | 3.0 |
| *A. mirum* C276T | 16 | 0.75 | 1.4 | 1.0 | 3.0 | 6.0 | 8.8 | 8.1 | 5.1 |
| *T. maritima* C277S | 17 | 0.75 | 1.4 | 1.0 | 1.3 | 2.6 | 4.2 | 4.8 | 4.2 |
| *T. maritima* C277T | 18 | 0.75 | 1.4 | 1.0 | 2.4 | 4.8 | 6.1 | 5.6 | 3.7 |
| *A. mirum* wild-type | 4 | 0.75 | 1.4 | 2.0 | 1.0 | 1.8 | 1.2 | 0.4 | 0.4 |
| *A. mirum* C276S | 14 | 0.75 | 1.4 | 2.0 | 5.3 | 6.7 | 4.8 | 1.8 | 1.2 |
| *A. mirum* C276T | 16 | 0.75 | 1.4 | 2.0 | 5.5 | 8.6 | 7.7 | 2.4 | 1.4 |
| *T. maritima* C277S | 17 | 0.75 | 1.4 | 2.0 | 2.9 | 4.2 | 5.0 | 3.4 | 2.0 |
| *T. maritima* C277T | 18 | 0.75 | 1.4 | 2.0 | 4.1 | 6.2 | 5.5 | 2.1 | 1.1 |

Example 17

Production of Peracetic Acid from Triacetin and Hydrogen Peroxide by CE-7 Esterase Variants Reactions (10 mL total volume) were run at 25° C. in potassium phosphate buffer (50 mM, pH 7.0) containing triacetin (10 mM), hydrogen peroxide (20 mM) and 0.5 μg/mL of CE-7 esterase from wild-type *Actinosynnema mirum* (SEQ ID NO: 4, prepared as described in Example 1), *Actinosyn-* nema mirum C276S variant (SEQ ID NO: 14, prepared as described in Example 13), *Actinosynnema mirum* C276T variant (SEQ ID NO: 16, prepared as described in Example 14), *T. maritima* C277S (SEQ ID NO: 17), and *T. maritima* C277T (SEQ ID NO: 18). Analysis of cell extracts containing CE-7 esterase by SDS-PAGE gels in combination with analysis of the gels using ImageJ, a public domain Java image processing program, was used to calculate the concentration of CE-7 esterase in cell extracts as a percentage of total soluble protein. Reactions were stirred for only the first 45 seconds of reaction to initially mix the reactants and enzyme. A comparative control reaction was run under identical conditions to that described immediately above using no added CE-7 esterase, where peracetic acid produced in the absence of added esterase was the result of chemical perhydrolysis of triacetin by hydrogen peroxide under the specified reaction conditions. Analysis of reaction samples for the production of peracetic acid followed the method described in Example 7 (Table 10).

TABLE 10

CE-7 perhydrolase variant-catalyzed production of peracetic acid (PAA) from triacetin and hydrogen peroxide in potassium phosphate buffer (50 mM, pH 7.0) at 25° C.

| CE-7 esterase source | SEQ ID NO | triacetin (mM) | $H_2O_2$ (mM) | CE-7 esterase variant (µg/mL) | PAA at 2 min (ppm) | PAA at 5 min (ppm) | PAA at 10 min (ppm) | PAA at 20 min (ppm) | PAA at 30 min (ppm) |
|---|---|---|---|---|---|---|---|---|---|
| control - no enzyme | | 10 | 20 | 0 | 3.1 | 8.0 | 2.6 | 4.1 | 4.0 |
| *A. mirum* wild-type | 4 | 10 | 20 | 0.5 | 8.1 | 11 | 19 | 34 | 46 |
| *A. mirum* C276S | 14 | 10 | 20 | 0.5 | 39 | 76 | 99 | 92 | 80 |
| *A. mirum* C276T | 16 | 10 | 20 | 0.5 | 26 | 60 | 96 | 118 | 115 |
| *T. maritima* C277S | 17 | 10 | 20 | 0.5 | 22 | 43 | 63 | 74 | 68 |
| *T. maritima* C277T | 18 | 10 | 20 | 0.5 | 29 | 58 | 96 | 131 | 132 |

Example 18

Production of Peracetic Acid from Triacetin and Hydrogen Peroxide by CE-7 Esterase Variants Reactions (10 mL total volume) were run at 25° C. in sodium carbonate buffer (20 mM, pH 10.5) containing triacetin (0.75 mM), hydrogen peroxide (1.4 mM, from sodium percarbonate) and either 1.0 µg/mL or 2.0 µg/mL of CE-7 esterase from wild-type *Actinosynnema mirum* (SEQ ID NO: 4, prepared as described in Example 1), *Actinosynnema mirum* C276S variant (SEQ ID NO: 14, prepared as described in Example 13), *Actinosynnema mirum* C276T variant (SEQ ID NO:16, prepared as described in Example 14), *T. maritima* C277S (SEQ ID NO: 17), and *T. maritima* C277T (SEQ ID NO: 18). Analysis of cell extracts containing CE-7 esterase by SDS-PAGE gels in combination with analysis of the gels using ImageJ, a public domain Java image processing program, was used to calculate the concentration of CE-7 esterase in cell extracts as a percentage of total soluble protein. Reactions were stirred for only the first 45 seconds of reaction to initially mix the reactants and enzyme. A comparative control reaction was run under identical conditions to that described immediately above using no added CE-7 esterase, where peracetic acid produced in the absence of added esterase was the result of chemical perhydrolysis of triacetin by hydrogen peroxide under the specified reaction conditions. Analysis of reaction samples for the production of peracetic acid followed the method described in Example 7 (Table 11).

TABLE 11

CE-7 perhydrolase variant-catalyzed production of peracetic acid (PAA) from triacetin and hydrogen peroxide in sodium carbonate buffer (20 mM, pH 10.5) at 25° C.

| CE-7 esterase source | SEQ ID NO | triacetin (mM) | $H_2O_2$ (mM) | CE-7 esterase variant (µg/mL) | PAA at 2 min (ppm) | PAA at 5 min (ppm) | PAA at 10 min (ppm) | PAA at 20 min (ppm) | PAA at 30 min (ppm) |
|---|---|---|---|---|---|---|---|---|---|
| control - no enzyme | | 0.75 | 1.4 | 0 | 1.3 | 2.7 | 4.7 | 7.7 | 9.7 |
| *A. mirum* wild-type | 4 | 0.75 | 1.4 | 1.0 | 2.0 | 3.6 | 5.4 | 6.8 | 7.5 |
| *A. mirum* C276S | 14 | 0.75 | 1.4 | 1.0 | 4.6 | 9.3 | 13.0 | 16.0 | 17.0 |
| *A. mirum* C276T | 16 | 0.75 | 1.4 | 1.0 | 5.3 | 11.1 | 17.1 | 21.1 | 23.1 |

TABLE 11-continued

CE-7 perhydrolase variant-catalyzed production of peracetic acid (PAA) from triacetin and hydrogen peroxide in sodium carbonate buffer (20 mM, pH 10.5) at 25° C.

| CE-7 esterase source | SEQ ID NO | triacetin (mM) | $H_2O_2$ (mM) | CE-7 esterase variant (μg/mL) | PAA at 2 min (ppm) | PAA at 5 min (ppm) | PAA at 10 min (ppm) | PAA at 20 min (ppm) | PAA at 30 min (ppm) |
|---|---|---|---|---|---|---|---|---|---|
| T. maritima C277S | 17 | 0.75 | 1.4 | 1.0 | 2.9 | 5.2 | 8.0 | 11.1 | 12.0 |
| T. maritima C277T | 18 | 0.75 | 1.4 | 1.0 | 3.4 | 6.2 | 9.5 | 13.2 | 14.5 |
| A. mirum wild-type | 4 | 0.75 | 1.4 | 2.0 | 2.1 | 3.8 | 5.2 | 6.3 | 6.5 |
| A. mirum C276S | 14 | 0.75 | 1.4 | 2.0 | 6.8 | 12.0 | 14.9 | 17.2 | 18.7 |
| A. mirum C276T | 16 | 0.75 | 1.4 | 2.0 | 8.6 | 16.0 | 20.7 | 24.4 | 26.1 |
| T. maritima C277S | 17 | 0.75 | 1.4 | 2.0 | 3.8 | 7.0 | 10.5 | 13.4 | 14.4 |
| T. maritima C277T | 18 | 0.75 | 1.4 | 2.0 | 4.7 | 8.4 | 12.8 | 16.5 | 17.9 |

What is claimed is:

1. A process for producing a peroxycarboxylic acid comprising:
   (a) providing a set of reaction components comprising:
      (1) at least one substrate selected from the group consisting of:
         (i) one or more esters having the structure

[X]$_m$R$_5$ wherein
         X=an ester group of the formula R$_6$—C(O)O;
         R$_6$=a C1 to C7 linear, branched or cyclic hydrocarbyl moiety, optionally substituted with hydroxyl groups or C1 to C4 alkoxy groups, wherein R$_6$ optionally comprises one or more ether linkages for R$_6$=C2 to C7;
         R$_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in R$_5$ individually comprises no more than one hydroxyl group or no more than one ester group or carboxylic acid group; wherein R$_5$ optionally comprises one or more ether linkages; m=an integer ranging from 1 to the number of carbon atoms in R$_5$; and wherein said esters have solubility in water of at least 5 ppm at 25° C.;

(ii) one or more glycerides having the structure

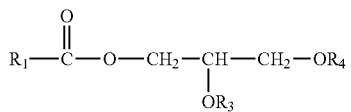

wherein R$_1$=a C1 to C21 straight chain or branched chain alkyl optionally substituted with an hydroxyl or a C1 to C4 alkoxy group and R$_3$ and R$_4$ are individually H or R$_1$C(O);

(iii) one or more esters of the formula:

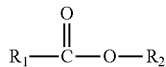

wherein R$_1$=a C1 to C7 straight chain or branched chain alkyl optionally substituted with an hydroxyl or a C1 to C4 alkoxy group and R$_2$=a C1 to C10 straight chain or branched chain alkyl, alkenyl, alkynyl, aryl, alkylaryl, alkylheteroaryl, heteroaryl, (CH$_2$CH$_2$O)$_n$, or (CH$_2$CH(CH$_3$)—O)$_n$H and n is 1 to 10;

(iv) one or more acylated monosaccharides, acylated disaccharides, or acylated polysaccharides; and (v) any combination of (i) through (iv);
(2) a source of peroxygen; and
(3) an enzyme catalyst comprising a polypeptide having perhydrolytic activity and an amino acid sequence having at least 80% identity to the amino acid sequence set forth in SEQ ID NO: 10, provided that the amino acid residue bound to the C-terminal side of the catalytic histidine is not glutamic acid;

(b) combining the set of reaction components under suitable reaction conditions whereby peroxycarboxylic acid is produced; and (c) optionally diluting the peroxycarboxylic acid produced in step (b).

2. The process of claim 1 further comprising the step of: d) contacting a hard surface or inanimate object with the peroxycarboxylic acid produced in step (b) or step (c); whereby said hard surface or said inanimate object is disinfected, bleached, destained or a combination thereof.

3. The process of claim 1 wherein the inanimate object is a medical instrument.

4. The process of claim 1 further comprising the step of: d) contacting an article of clothing or a textile with peroxycarboxylic acid produced in step (b) or step (c); whereby the article of clothing or textile receives a benefit.

5. The process of claim 4 wherein the benefit is selected from the group consisting of a disinfecting, sanitizing, bleaching, destaining, deodorizing, and combinations thereof.

6. The process of claim 1 further comprising the step of: d) contacting wood pulp or paper pulp with peroxycarboxylic acid produced in step (b) or step (c); whereby the wood pulp or paper pulp is bleached.

7. The process of claim 1 wherein the substrate is selected from the group consisting of: monoacetin; diacetin; triacetin; monopropionin; dipropionin; tripropionin; monobutyrin; dibutyrin; tributyrin; glucose pentaacetate; β-D-galactose pentaacetate, sorbitol hexaacetate, sucrose octaacetate, xylose tetraacetate; acetylated xylan; acetylated xylan fragments; β-D-ribofuranose-1,2,3,5-tetraacetate, tri-O-acetyl-D-galactal; tri-O-acetyl-D-glucal, monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol, 4-acetoxybenzoic acid; and mixtures thereof.

8. The process of claim 7 wherein the substrate is triacetin.

9. The process of claim 1 wherein the peroxycarboxylic acid produced is peracetic acid, perpropionic acid, perbutyric acid, perlactic acid, perglycolic acid, permethoxyacetic acid, per-β-hydroxybutyric acid, or mixtures thereof.

10. The process of claim 1 wherein the enzyme catalyst is in the form of a microbial cell, a permeabilized microbial cell, a microbial cell extract, a partially purified enzyme, or a purified enzyme.

11. A composition comprising:
(a) a set of reaction components comprising:
(1) at least one substrate selected from the group consisting of:
(i) one or more esters having the structure $[X]_m R_5$ wherein
X=an ester group of the formula $R_6-C(O)O$;
$R_6$=a C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m=an integer ranging from 1 to the number of carbon atoms in $R_5$; and wherein said esters have solubility in water of at least 5 ppm at 25° C.;

(ii) one or more glycerides having the structure

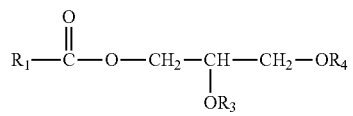

wherein $R_1$=a C1 to C21 straight chain or branched chain alkyl optionally substituted with an hydroxyl or a C1 to C4 alkoxy group and $R_3$ and $R_4$ are individually H or $R_1C(O)$;

(iii) one or more esters of the formula:

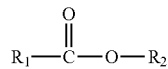

wherein $R_1$=a C1 to C7 straight chain or branched chain alkyl optionally substituted with an hydroxyl or a C1 to C4 alkoxy group and $R_2$=a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10;

(iv) one or more acylated monosaccharides, acylated disaccharides, or acylated polysaccharides; and (v) any combination of (i) through (iv);

(2) a source of peroxygen; and (3) an enzyme catalyst comprising a polypeptide having perhydrolytic activity and an amino acid sequence having at least 90% identity to the amino acid sequence set forth in SEQ ID NO: 10, provided that the amino acid residue bound to the C-terminal side of the catalytic histidine is not glutamic acid;

(b) at least one peroxycarboxylic acid formed upon combining the set of reaction components of (a).

12. A peracid generation and delivery system comprising:
(a) a first compartment comprising:
(1) an enzyme catalyst comprising a polypeptide having perhydrolytic activity and an amino acid sequence having at least 90% identity to the amino acid sequence set forth in SEQ ID NO: 10, provided that the amino acid residue bound to the C-terminal side of the catalytic histidine is not glutamic acid;

(2) at least one substrate selected from the group consisting of:
(i) one or more esters having the structure

wherein
X=an ester group of the formula $R_6$—C(O)O;
$R_6$=a C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;
m=an integer ranging from 1 to the number of carbon atoms in $R_5$; and
wherein said esters have solubility in water of at least 5 ppm at 25° C.;
(ii) one or more glycerides having the structure

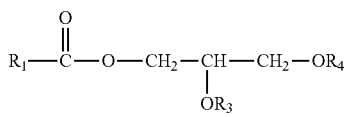

wherein $R_1$=a C1 to C21 straight chain or branched chain alkyl optionally substituted with an hydroxyl or a C1 to C4 alkoxy group and $R_3$ and $R_4$ are individually H or $R_1$C(O);
(iii) one or more esters of the formula:

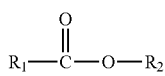

wherein $R_1$=a C1 to C7 straight chain or branched chain alkyl optionally substituted with an hydroxyl or a C1 to C4 alkoxy group and $R_2$=a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)$—$O)_nH$ and n is 1 to 10;
(iv) one or more acylated monosaccharides, acylated disaccharides, or acylated polysaccharides; and
(v) any combination of (i) through (iv);
(3) an optional buffer; and
(b) a second compartment comprising
(1) source of peroxygen;
(2) a peroxide stabilizer; and
(3) an optional buffer.

13. The peracid generation and delivery system of claim 12 wherein the substrate comprises triacetin.

14. A laundry care composition comprising
(a) a polypeptide having perhydrolytic activity and an amino acid sequence having at least 90% identity to the amino acid sequence set forth in SEQ ID NO: 10, provided that the amino acid residue bound to the C-terminal side of the catalytic histidine is not glutamic acid;
(b) at least one substrate selected from the group consisting of:
(i) one or more esters having the structure

wherein
X=an ester group of the formula $R_6$—C(O)O;
$R_6$=a C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group;
wherein $R_5$ optionally comprises one or more ether linkages;
m=an integer ranging from 1 to the number of carbon atoms in $R_5$; and
wherein said esters have solubility in water of at least 5 ppm at 25° C.;
(ii) one or more glycerides having the structure

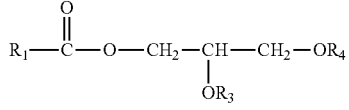

wherein $R_1$=a C1 to C21 straight chain or branched chain alkyl optionally substituted with an hydroxyl or a C1 to C4 alkoxy group and $R_3$ and $R_4$ are individually H or $R_1$C(O);
(iii) one or more esters of the formula:

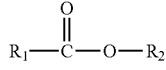

wherein $R_1$=a C1 to C7 straight chain or branched chain alkyl optionally substituted with an hydroxyl or a C1 to C4 alkoxy group and $R_2$=a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)$—$O)_nH$ and n is 1 to 10;
(iv) one or more acylated monosaccharides, acylated disaccharides, or acylated polysaccharides; and
(v) any combination of (i) through (iv);
(c) a source of peroxygen; and
(d) at least one surfactant.

15. A personal care product comprising a polypeptide having perhydrolytic activity, said polypeptide having an amino acid sequence having at least 90% identity to the amino acid sequence set forth in SEQ ID NO:10, provided that the amino acid residue bound to the C-terminal side of the catalytic histidine is not glutamic acid.

16. The personal care product of claim 15 wherein the product is a shampoo, a body lotion, a shower gel, a topical moisturizer, a toothpaste, a toothgel, a mouthwash, a mouthrinse, an anti-plaque rinse or a topical cleanser.

* * * * *

SEQUENCE LISTING

<160> NUMBER OF SEQ ID NOS: 18

<210> SEQ ID NO 1
<211> LENGTH: 978
<212> TYPE: DNA
<213> ORGANISM: Thermotoga maritima

<400> SEQUENCE: 1

```
atggcgttct tcgacctgcc tctggaagaa ctgaagaaat accgtccaga gcgttacgaa      60
gagaaggact tcgacgagtt ctgggaggaa actctggcgg agagcgaaaa gtttccgctg     120
gacccagtgt tcgagcgtat ggaatctcac ctgaaaaccg tggaggcata tgacgttact     180
ttttctggtt accgtggcca gcgtatcaaa ggctggctgc tggttccgaa actggaggaa     240
gaaaaactgc cgtgcgtagt tcagtacatc ggttacaacg gtggccgtgg ctttccgcac     300
gattggctgt tctggccgtc tatgggctac atttgcttcg tcatggatac tcgtggtcag     360
ggttccggct ggctgaaagg cgatactccg gattatccgg agggcccggt agacccgcag     420
taccctggct tcatgacgcg tggtattctg atccgcgta cctattacta tcgccgcgtt     480
tttaccgatg cagttcgtgc cgtagaggcc gcggcttctt ccctcaggt tgaccaggag     540
cgtattgtta tcgctggtgg ctcccagggt ggcggcatcg ccctggcggt atctgcgctg     600
agcaagaaag ctaaggcact gctgtgtgac gtcccgttcc tgtgtcactt ccgtcgcgct     660
gttcagctgg tagatacccca tccgtacgcg gagattacta acttcctgaa aactcaccgc     720
gacaaagaag aaatcgtttt ccgcacccg tcctatttcg acggcgttaa cttcgcggct     780
cgtgcaaaaa ttccggcact gttctctgtt ggtctgatgg acaacatctg ccctccttct     840
accgttttcg cggcatataa ctattatgcg ggtccgaaag aaatccgtat ctatccgtac     900
aacaaccacg aaggcggtgg tagctttcag gctgttgaac aagtgaaatt cctgaagaaa     960
ctgtttgaga agggctaa                                                    978
```

<210> SEQ ID NO 2
<211> LENGTH: 325
<212> TYPE: PRT
<213> ORGANISM: Thermotoga maritima

<400> SEQUENCE: 2

```
Met Ala Phe Phe Asp Leu Pro Leu Glu Glu Leu Lys Lys Tyr Arg Pro
 1               5                  10                  15

Glu Arg Tyr Glu Glu Lys Asp Phe Asp Glu Phe Trp Glu Glu Thr Leu
             20                  25                  30

Ala Glu Ser Glu Lys Phe Pro Leu Asp Pro Val Phe Glu Arg Met Glu
```

```
            35                  40                  45
Ser His Leu Lys Thr Val Glu Ala Tyr Asp Val Thr Phe Ser Gly Tyr
 50                  55                  60

Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 3
<211> LENGTH: 963
<212> TYPE: DNA
<213> ORGANISM: Actinosynnema mirum

<400> SEQUENCE: 3
atgccatggt tgacctgcc agaagcagag ctcgcgcaat accgcacccc gacgccggag      60
ccagcgggct tggacgcgtg gtgggcggag cgtctggcgg aggcgcgtgc gctggccgaa     120
ccggttacca gcaccccgca cgaagagtcc gcgtatggtc cgctgggcgt ccgtgacgtg     180
gaattttccg cgcactggg cgatcgcgtc cgcgcgtggc acctgcgtcc ggctggcgat     240
gacccgctgc cgacggcggt cgtattcatt ggttacggtg gtggtcgtgg tacccccgacc    300 gagcatgcct ggctggccgc agcaggttac ggcgtgctgg ttgtcgatac ccgcggtcag     360
ggtggtcgtt ggacgaccgg tgcgacggct gattctgcgc cgagcggtcc gagccatccg     420
ggtttcatga ctcgcggtat tacgagcccg gagggctatt actatacccg tctgatgacc     480
```

-continued

```
gatgctgcac tggcggtgga cgttgcagcc ggcctggatg gcgtggatcc ggaacgtatc    540
gccgtgctgg gtgcatcgca aggcggtggc ctggcgttgg cagccgcagc tctgaacccg    600
accaaagtta aggtctgcca cgccgatgtt ccgtttctgt gcgacttcca gcgtgccatt    660
acgctgacgg gtgcggaccc gtacgcggag atcgcgaatt tcttgtctca taatgtcgcc    720
ctggtgaagc aggttcgtga aaccctgact tacgtggacg cggctctgct gagccgtcgt    780
atcaccgcaa ctagcctgtt gagcgcaggt ctgatggacg aagtttgtcc tccgagcacc    840
gtgtttgcgg cgtataacga gatcacggct cctaaacgta ttgaggtttt cccgtttagc    900
ggccacgcgg ttccgcgcac ccacgacgaa gtcaaattga agcatctgcg cgagcacctg    960
taa                                                                 963
```

<210> SEQ ID NO 4
<211> LENGTH: 320
<212> TYPE: PRT
<213> ORGANISM: Actinosynnema mirum

<400> SEQUENCE: 4

```
Met Pro Trp Phe Asp Leu Pro Glu Ala Glu Leu Ala Gln Tyr Arg Thr
1               5                   10                  15

Pro Thr Pro Glu Pro Ala Gly Leu Asp Ala Trp Trp Ala Glu Arg Leu
            20                  25                  30

Ala Glu Ala Arg Ala Leu Ala Glu Pro Val Thr Ser Thr Pro His Glu
        35                  40                  45

Glu Ser Ala Tyr Gly Pro Leu Gly Val Arg Asp Val Glu Phe Ser Gly
    50                  55                  60

Ala Leu Gly Asp Arg Val Arg Ala Trp His Leu Arg Pro Ala Gly Asp
65                  70                  75                  80

Asp Pro Leu Pro Thr Ala Val Val Phe Ile Gly Tyr Gly Gly Gly Arg
                85                  90                  95

Gly Thr Pro Thr Glu His Ala Trp Leu Ala Ala Gly Tyr Gly Val
            100                 105                 110

Leu Val Val Asp Thr Arg Gly Gln Gly Gly Arg Trp Thr Thr Gly Ala
        115                 120                 125

Thr Ala Asp Ser Ala Pro Ser Gly Pro Ser His Pro Gly Phe Met Thr
    130                 135                 140

Arg Gly Ile Thr Ser Pro Glu Gly Tyr Tyr Tyr Thr Arg Leu Met Thr
145                 150                 155                 160

Asp Ala Ala Leu Ala Val Asp Val Ala Ala Gly Leu Asp Gly Val Asp
                165                 170                 175

Pro Glu Arg Ile Ala Val Leu Gly Ala Ser Gln Gly Gly Gly Leu Ala
            180                 185                 190

Leu Ala Ala Ala Ala Leu Asn Pro Thr Lys Val Lys Val Cys His Ala
        195                 200                 205

Asp Val Pro Phe Leu Cys Asp Phe Gln Arg Ala Ile Thr Leu Thr Gly
    210                 215                 220

Ala Asp Pro Tyr Ala Glu Ile Ala Asn Phe Leu Ser His Asn Val Ala
225                 230                 235                 240

Leu Val Lys Gln Val Arg Glu Thr Leu Thr Tyr Val Asp Ala Ala Leu
                245                 250                 255

Leu Ser Arg Arg Ile Thr Ala Thr Ser Leu Leu Ser Ala Gly Leu Met
            260                 265                 270

Asp Glu Val Cys Pro Pro Ser Thr Val Phe Ala Ala Tyr Asn Glu Ile
```

```
            275                 280                 285
Thr Ala Pro Lys Arg Ile Glu Val Phe Pro Phe Ser Gly His Ala Val
        290                 295                 300

Pro Arg Thr His Asp Glu Val Lys Leu Lys His Leu Arg Glu His Leu
305                 310                 315                 320
```

<210> SEQ ID NO 5
<211> LENGTH: 990
<212> TYPE: DNA
<213> ORGANISM: Propionibacterium acnes

<400> SEQUENCE: 5

```
atgccgctga ccgacttggg tattgacgaa gcgagaactt acagaccgaa cgtgccagag    60
ccggatggtt ttgatagctt tgggcggaa  accctggatg agtacagcgg tgttccgcag   120
gatctgaccg cggtgccgtt cgacaaccgt caagccctga ttgacacgtg ggacctgtcg   180
tgggctggct atcataactc tcgcgtcagc ggctggctgc acgccccagc ggccgtgaac   240
ggtccgctgc cgttggtcat tgaatacctg ggttacagca gcagccgtgg tgtaccgatt   300
ggtagcgtgt tcgccgctgc gggctatgcg cacatcgtcg ttgacccgcg tggtcagggt   360
tggggtcacc cgacgttgac cgagaattgc ccggacgtgc atgacggctc cggcgctcct   420
ggttttatga cccaaagcct gagcgacccg cacggtcatt actatcgtcg cctgttcacg   480
gatgcgttcc gctgtctgca agcagcacgt gagatggaat ggtggatcc  gacgcgtatc   540
gctgttctgg ccactcccca aggtggtggc caggcgattg cggtgtgtgc gctggcggcc   600
atgcgcggca tcaagctggc gggtgcgttc gttgacgtcc cgttcctgtg ccatatccgt   660
cgtagctgcg acatcgcaac ggatggtccg tacctggagg ttgttcgtta cctggcagcg   720
cacccgagcc tgtgtggccg tgcttttcag accctgggct acttcgacgg cttgcacttt   780
gcacgtcgtg cccgcacctc cacctggttt tctgtcgcga tgatggatca ggcagtccct   840
ccgagcagcg tttgggcagc gtataatgcg tgggcgatg  gtatggttgc agataaacac   900
atcgccgttt atccgtttgc aggtcatgca gcgggcgagg atgtccaacg ctggaatcag   960
ctgggtgtgc tggcccagct gttcagctaa                                    990
```

<210> SEQ ID NO 6
<211> LENGTH: 329
<212> TYPE: PRT
<213> ORGANISM: Propionibacterium acnes

<400> SEQUENCE: 6

```
Met Pro Leu Thr Asp Leu Gly Ile Asp Glu Ala Arg Thr Tyr Arg Pro
1               5                   10                  15

Asn Val Pro Glu Pro Asp Gly Phe Asp Ser Phe Trp Ala Glu Thr Leu
            20                  25                  30

Asp Glu Tyr Ser Gly Val Pro Gln Asp Leu Thr Ala Val Pro Phe Asp
        35                  40                  45

Asn Arg Gln Ala Leu Ile Asp Thr Trp Asp Leu Ser Trp Ala Gly Tyr
    50                  55                  60

His Asn Ser Arg Val Ser Gly Trp Leu His Ala Pro Ala Val Asn
65                  70                  75                  80

Gly Pro Leu Pro Leu Val Ile Glu Tyr Leu Gly Tyr Ser Ser Ser Arg
                85                  90                  95

Gly Val Pro Ile Gly Ser Val Phe Ala Ala Gly Tyr Ala His Ile
            100                 105                 110
```

```
Val Val Asp Pro Arg Gly Gln Gly Trp Gly His Pro Thr Leu Thr Glu
            115                 120                 125

Asn Cys Pro Asp Val His Asp Gly Ser Gly Ala Pro Gly Phe Met Thr
        130                 135                 140

Gln Ser Leu Ser Asp Pro His Gly His Tyr Tyr Arg Arg Leu Phe Thr
145                 150                 155                 160

Asp Ala Phe Arg Cys Leu Gln Ala Ala Arg Glu Met Glu Leu Val Asp
                165                 170                 175

Pro Thr Arg Ile Ala Val Leu Gly His Ser Gln Gly Gly Gly Gln Ala
            180                 185                 190

Ile Ala Val Cys Ala Leu Ala Ala Met Arg Gly Ile Lys Leu Ala Gly
        195                 200                 205

Ala Phe Val Asp Val Pro Phe Leu Cys His Ile Arg Arg Ser Cys Asp
210                 215                 220

Ile Ala Thr Asp Gly Pro Tyr Leu Glu Val Val Arg Tyr Leu Ala Ala
225                 230                 235                 240

His Pro Ser Leu Cys Gly Arg Ala Phe Gln Thr Leu Gly Tyr Phe Asp
                245                 250                 255

Gly Leu His Phe Ala Arg Arg Ala Arg Thr Ser Thr Trp Phe Ser Val
            260                 265                 270

Ala Met Met Asp Gln Ala Val Pro Pro Ser Ser Val Trp Ala Ala Tyr
        275                 280                 285

Asn Ala Trp Gly Asp Gly Met Val Ala Asp Lys His Ile Ala Val Tyr
        290                 295                 300

Pro Phe Ala Gly His Ala Ala Gly Glu Asp Val Gln Arg Trp Asn Gln
305                 310                 315                 320

Leu Gly Val Leu Ala Gln Leu Phe Ser
                325

<210> SEQ ID NO 7
<211> LENGTH: 969
<212> TYPE: DNA
<213> ORGANISM: Streptococcus equi

<400> SEQUENCE: 7
atgatcgaaa ccatgagctt agaagagatg atgtcctaca gaggccgcca cgaagtcccg      60
aaagatttcg accattttg ggagacttgc attaaggaaa accaggcggc atcgtatcag     120
ctggaccaga aggattttgg cctggacttc gccgactgtt atgaactgcg tttcaagggc     180
agcaacggta gcaccattta cgctaaatgt gttttccga aagcgaaaca actggtcccg     240
gtggtgttct atttccacgg ttatcagggt cagagcccgg actggagcga ccaattcaat     300
tacctggcgg ctggttacgc cgttgtcagc atggacgttc gtggtcaggc gggctactcc     360
caggatctgg tcaatttga tggtatcacc gtgaaaggtc aagttatccg tggtatgacc     420
tctggcccgg agcaattgtt ttacaaggat gtgtacctgg acgtatatca actgatcgac     480
attgttagcg cgtttgcgcg tgtggatgat agccgcttgt actcttatgg ctggagccag     540
ggcggtgcgc tgagcctgat cgcagcagcc ttgcatccga aaatcgcaaa accgtcgcc      600 gtttacccgt tcctgagcga ctttaagcgt gtgctggagc tgggtaacca cagcgagccg     660
tatgacgagc tgtttcgtta cttcaaatac cacgacccat tcacgatac ggaagcggag      720 gtgctgggta atctggcgta tatcgacgtc aaaaacttcg cacatctgat tacgtgcccg     780
gtcgtgatgt tgacgtgcat ggaggatgtt atttgcccgc cttccaccca gttcgcgatc     840
ttcaatcgcc tggcgacggc agataagtgt cacaagctga ttccggacta cggtcacgac     900
```

-continued

```
ccaatgggcg tcaaagttaa ggatttcatt ttcgatcaac tgaccggcag ccatttttacc    960 aaggcttaa                                                              969
```

<210> SEQ ID NO 8
<211> LENGTH: 322
<212> TYPE: PRT
<213> ORGANISM: Streptococcus equi

<400> SEQUENCE: 8

```
Met Ile Glu Thr Met Ser Leu Glu Glu Met Met Ser Tyr Arg Gly Arg
1               5                   10                  15

His Glu Val Pro Lys Asp Phe Asp His Phe Trp Glu Thr Cys Ile Lys
            20                  25                  30

Glu Asn Gln Ala Ala Ser Tyr Gln Leu Asp Gln Lys Asp Phe Gly Leu
        35                  40                  45

Asp Phe Ala Asp Cys Tyr Glu Leu Arg Phe Lys Gly Ser Asn Gly Ser
    50                  55                  60

Thr Ile Tyr Ala Lys Cys Val Phe Pro Lys Ala Lys Gln Leu Val Pro
65                  70                  75                  80

Val Val Phe Tyr Phe His Gly Tyr Gln Gly Gln Ser Pro Asp Trp Ser
                85                  90                  95

Asp Gln Phe Asn Tyr Leu Ala Ala Gly Tyr Ala Val Val Ser Met Asp
            100                 105                 110

Val Arg Gly Gln Ala Gly Tyr Ser Gln Asp Leu Gly Gln Phe Asp Gly
        115                 120                 125

Ile Thr Val Lys Gly Gln Val Ile Arg Gly Met Thr Ser Gly Pro Glu
    130                 135                 140

Gln Leu Phe Tyr Lys Asp Val Tyr Leu Asp Val Tyr Gln Leu Ile Asp
145                 150                 155                 160

Ile Val Ser Ala Phe Ala Arg Val Asp Asp Ser Arg Leu Tyr Ser Tyr
                165                 170                 175

Gly Trp Ser Gln Gly Gly Ala Leu Ser Leu Ile Ala Ala Ala Leu His
            180                 185                 190

Pro Lys Ile Ala Lys Thr Val Ala Val Tyr Pro Phe Leu Ser Asp Phe
        195                 200                 205

Lys Arg Val Leu Glu Leu Gly Asn His Ser Glu Pro Tyr Asp Glu Leu
    210                 215                 220

Phe Arg Tyr Phe Lys Tyr His Asp Pro Phe His Asp Thr Glu Ala Glu
225                 230                 235                 240

Val Leu Gly Asn Leu Ala Tyr Ile Asp Val Lys Asn Phe Ala His Leu
                245                 250                 255

Ile Thr Cys Pro Val Val Met Leu Thr Cys Met Glu Asp Val Ile Cys
            260                 265                 270

Pro Pro Ser Thr Gln Phe Ala Ile Phe Asn Arg Leu Ala Thr Ala Asp
        275                 280                 285

Lys Cys His Lys Leu Ile Pro Asp Tyr Gly His Asp Pro Met Gly Val
    290                 295                 300

Lys Val Lys Asp Phe Ile Phe Asp Gln Leu Thr Gly Ser His Phe Thr
305                 310                 315                 320

Lys Ala
```

<210> SEQ ID NO 9
<211> LENGTH: 978
<212> TYPE: DNA

<213> ORGANISM: Stackebrandtia nassauensis

<400> SEQUENCE: 9

```
atgccacttt tgatttccc acttgacgaa ctgcgtgcgt acagaccgga gccggacgaa      60
ccgcaggact cgacgcatt ttgggaccgc acctccgaag tggcggaccg tcacccgctg     120
gatgtgcgcc tgaccccgca accgggtcac ctgggtttgg tggatgtgtg ggatgttcgt    180
tttgcgggtt ggaacggcga cccgatcaac gcatggctga tcgcgcctgc cggtgcaagc   240
cgtgtgggct gcgtggtcac ctacattggt tatcatggcg gtcgcggctt ccgcaccaa    300
catctgcgct ggccggtcgc gggctgggcg acgctggttg ttgatacgcg cggtcagggt   360
gcgagcgcca gcgcgagctc tggcgtcacg ggtgatccgc acggtagcga gtttggccat   420
gctccgggta tgctgaccaa gggtatcctg gatccggatg agtactacta tcgtcgtgtt    480
ttcactgacg cggctcgcgc agtggatgtt gccgcgagcc tggacattgt tgacgagagc   540
cgtattgtcg ttagcggtca ttctcagggt ggcggtatcg cgcaagcggt tagcgcactg   600
cgtccgggcg tggcagcggc tttggtaaat gaaccgttcc tgtgtcactt tcgtcgtagc   660
tgtgagattg cgagcacggg tccgtacccg gaactggtcg cattcctggg tgcgcagcgt   720
gacctggagc agcgcgtttt cgctacccctg tcctatttcg aaggcatgag cttcgcctcg   780
cgtgcccaag cgcctgcctt gtatagcgtg gcactgatgg ataccacgtg cccaccgagc   840
accgtctttg cggcttacaa tcgttgggcc ggtccgaaag acatcgaggt ctggccgtgg   900
aacggtcact ccggtggtga aggctatcac gcacaacgtc agctggagtg gctgagcgag   960
cgcttcggca ccggctaa                                                 978
```

<210> SEQ ID NO 10
<211> LENGTH: 325
<212> TYPE: PRT
<213> ORGANISM: Stackebrandtia nassauensis

<400> SEQUENCE: 10

```
Met Pro Leu Phe Asp Phe Pro Leu Asp Glu Leu Arg Ala Tyr Arg Pro
1               5                   10                  15

Glu Pro Asp Glu Pro Gln Asp Phe Asp Ala Phe Trp Asp Arg Thr Ser
            20                  25                  30

Glu Val Ala Asp Arg His Pro Leu Asp Val Arg Leu Thr Pro Gln Pro
        35                  40                  45

Gly His Leu Gly Leu Val Asp Val Trp Asp Val Arg Phe Ala Gly Trp
    50                  55                  60

Asn Gly Asp Pro Ile Asn Ala Trp Leu Ile Ala Pro Ala Gly Ala Ser
65                  70                  75                  80

Arg Val Gly Cys Val Val Thr Tyr Ile Gly Tyr His Gly Gly Arg Gly
                85                  90                  95

Phe Pro His Gln His Leu Arg Trp Pro Val Ala Gly Trp Ala Thr Leu
            100                 105                 110

Val Val Asp Thr Arg Gly Gln Gly Ala Ser Ala Ser Ala Ser Ser Gly
        115                 120                 125

Val Thr Gly Asp Pro His Gly Ser Glu Phe His Ala Pro Gly Met
    130                 135                 140

Leu Thr Lys Gly Ile Leu Asp Pro Asp Glu Tyr Tyr Tyr Arg Arg Val
145                 150                 155                 160

Phe Thr Asp Ala Ala Arg Ala Val Asp Val Ala Ala Ser Leu Asp Ile
                165                 170                 175
```

```
Val Asp Glu Ser Arg Ile Val Val Ser Gly His Ser Gln Gly Gly
        180                 185                 190

Ile Ala Gln Ala Val Ser Ala Leu Arg Pro Gly Val Ala Ala Leu
        195                 200                 205

Val Asn Glu Pro Phe Leu Cys His Phe Arg Arg Ser Cys Glu Ile Ala
        210                 215                 220

Ser Thr Gly Pro Tyr Pro Glu Leu Val Ala Phe Leu Gly Ala Gln Arg
225                 230                 235                 240

Asp Leu Glu Gln Arg Val Phe Ala Thr Leu Ser Tyr Phe Glu Gly Met
                245                 250                 255

Ser Phe Ala Ser Arg Ala Gln Ala Pro Ala Leu Tyr Ser Val Ala Leu
            260                 265                 270

Met Asp Thr Thr Cys Pro Pro Ser Thr Val Phe Ala Ala Tyr Asn Arg
        275                 280                 285

Trp Ala Gly Pro Lys Asp Ile Glu Val Trp Pro Trp Asn Gly His Ser
        290                 295                 300

Gly Gly Glu Gly Tyr His Ala Gln Arg Gln Leu Glu Trp Leu Ser Glu
305                 310                 315                 320

Arg Phe Gly Thr Gly
                325

<210> SEQ ID NO 11
<211> LENGTH: 978
<212> TYPE: DNA
<213> ORGANISM: Streptococcus agalactiae

<400> SEQUENCE: 11
atgattgaaa cgatgagctt ggatgacatg cgtgaatact tgggtcaaga tcaaatcccg      60
gaggattttg acgactttg gaagaaacag accatgaagt accaaggcaa cattgagtat     120
cgcctggata gaaagactt caacatcacc tttgcgcagg cgtacgacct gcatttcaaa     180
ggttcgaaca attccattgt gtacgcgaaa tgtctgtttc gaaaacgaa taagccgtat     240
ccggtcgtgt tctacttcca cggctaccaa aaccaaagcc cggattggtc tgaccagctg     300
aattacgttg cagcgggcta tggtgtcgtc agcatggacg ttcgcggtca ggctggtcag     360
tctcaggata agggccactt cgatggtatt actgtcaaag ccaaatcgt tcgtggcatg     420
atcagcggtc cgaatcactt gttctacaag gacatttatc tggacgtgtt caactgatt     480
gatatcatcg caaccctgga gtccgtagac agcaaccagt tgtacagcta tggttggagc     540
caaggtggtg cgctggcact gattgcggct gcgctgaacc caaaaatcgt taaaaccgtg     600
gccgtttatc cgtttctgag cgatttccgt cgcgtgctgg acctgggcgg tgtgagcgag     660
ccgtacgacg aactgttccg ttacttcaag tatagcgatc cgttccacaa gacggaaaac     720
aatgttttga aaaccctggc atatatcgac gtcaagaatt ttgcgcatcg tattagctgc     780
ccggttgttc tgctgaccgc cctgaaagac gacatttgcc cgcctagcac ccagtttgcc     840
atcttcaatc gtctgacttc cacgaaaaag cacctgctgc tgccagatta cggtcatgat     900
ccgatgaccg tgcaggtcaa ggaccacatc ttcgatcagc tgaccggcag ccaatttacg     960
aagcagaaaa ttgagtaa                                                   978

<210> SEQ ID NO 12
<211> LENGTH: 325
<212> TYPE: PRT
<213> ORGANISM: Streptococcus agalactiae

<400> SEQUENCE: 12
```

```
Met Ile Glu Thr Met Ser Leu Asp Asp Met Arg Glu Tyr Leu Gly Gln
1               5                   10                  15

Asp Gln Ile Pro Glu Asp Phe Asp Phe Trp Lys Lys Gln Thr Met
            20                  25                  30

Lys Tyr Gln Gly Asn Ile Glu Tyr Arg Leu Asp Lys Lys Asp Phe Asn
        35                  40                  45

Ile Thr Phe Ala Gln Ala Tyr Asp Leu His Phe Lys Gly Ser Asn Asn
    50                  55                  60

Ser Ile Val Tyr Ala Lys Cys Leu Phe Pro Lys Thr Asn Lys Pro Tyr
65                  70                  75                  80

Pro Val Val Phe Tyr Phe His Gly Tyr Gln Asn Gln Ser Pro Asp Trp
                85                  90                  95

Ser Asp Gln Leu Asn Tyr Val Ala Ala Gly Tyr Gly Val Val Ser Met
            100                 105                 110

Asp Val Arg Gly Gln Ala Gly Gln Ser Gln Asp Lys Gly His Phe Asp
        115                 120                 125

Gly Ile Thr Val Lys Gly Gln Ile Val Arg Gly Met Ile Ser Gly Pro
130                 135                 140

Asn His Leu Phe Tyr Lys Asp Ile Tyr Leu Asp Val Phe Gln Leu Ile
145                 150                 155                 160

Asp Ile Ile Ala Thr Leu Glu Ser Val Asp Ser Asn Gln Leu Tyr Ser
                165                 170                 175

Tyr Gly Trp Ser Gln Gly Gly Ala Leu Ala Leu Ile Ala Ala Ala Leu
            180                 185                 190

Asn Pro Lys Ile Val Lys Thr Val Ala Val Tyr Pro Phe Leu Ser Asp
        195                 200                 205

Phe Arg Arg Val Leu Asp Leu Gly Gly Val Ser Glu Pro Tyr Asp Glu
210                 215                 220

Leu Phe Arg Tyr Phe Lys Tyr Ser Asp Pro Phe His Lys Thr Glu Asn
225                 230                 235                 240

Asn Val Leu Lys Thr Leu Ala Tyr Ile Asp Val Lys Asn Phe Ala His
                245                 250                 255

Arg Ile Ser Cys Pro Val Val Leu Leu Thr Ala Leu Lys Asp Asp Ile
            260                 265                 270

Cys Pro Pro Ser Thr Gln Phe Ala Ile Phe Asn Arg Leu Thr Ser Thr
        275                 280                 285

Lys Lys His Leu Leu Leu Pro Asp Tyr Gly His Asp Pro Met Thr Val
290                 295                 300

Gln Val Lys Asp His Ile Phe Asp Gln Leu Thr Gly Ser Gln Phe Thr
305                 310                 315                 320

Lys Gln Lys Ile Glu
                325
```

<210> SEQ ID NO 13
<211> LENGTH: 963
<212> TYPE: DNA
<213> ORGANISM: artificial sequence
<220> FEATURE:
<223> OTHER INFORMATION: synthetic construct

<400> SEQUENCE: 13

```
atgccatggt tgacctgcc agaagcagag ctcgcgcaat accgcacccc gacgccggag     60
ccagcgggct tggacgcgtg gtgggcggag cgtctggcgg aggcgcgtgc gctggccgaa    120
ccggttacca gcaccccgca cgaagagtcc gcgtatggtc cgctgggcgt ccgtgacgtg    180
```

```
gaattttccg gcgcactggg cgatcgcgtc cgcgcgtggc acctgcgtcc ggctggcgat    240
gacccgctgc cgacggcggt cgtattcatt ggttacggtg gtggtcgtgg taccccgacc    300
gagcatgcct ggctggccgc agcaggttac ggcgtgctgg ttgtcgatac ccgcggtcag    360
ggtggtcgtt ggacgaccgg tgcgacggct gattctgcgc cgagcggtcc gagccatccg    420
ggtttcatga ctcgcggtat tacgagcccg gagggctatt actatacccg tctgatgacc    480
gatgctgcac tggcggtgga cgttgcagcc ggcctggatg gcgtggatcc ggaacgtatc    540
gccgtgctgg gtgcatcgca aggcggtggc ctggcgttgg cagccgcagc tctgaacccg    600
accaaagtta aggtctgcca cgccgatgtt ccgtttctgt gcgacttcca gcgtgccatt    660
acgctgacgg gtgcggaccc gtacgcggag atcgcgaatt tcttgtctca taatgtcgcc    720
ctggtgaagc aggttcgtga aaccctgact tacgtggacg cggctctgct gagccgtcgt    780
atcaccgcaa ctagcctgtt gagcgcaggt ctgatggacg aagttagccc tccgagcacc    840
gtgtttgcgg cgtataacga gatcacggct cctaaacgta ttgaggtttt cccgtttagc    900
ggccacgcgg ttccgcgcac ccacgacgaa gtcaaattga agcatctgcg cgagcacctg    960
taa                                                                  963

<210> SEQ ID NO 14
<211> LENGTH: 320
<212> TYPE: PRT
<213> ORGANISM: artificial sequence
<220> FEATURE:
<223> OTHER INFORMATION: synthetic construct

<400> SEQUENCE: 14

Met Pro Trp Phe Asp Leu Pro Glu Ala Glu Leu Ala Gln Tyr Arg Thr
1               5                   10                  15

Pro Thr Pro Glu Pro Ala Gly Leu Asp Ala Trp Trp Ala Glu Arg Leu
            20                  25                  30

Ala Glu Ala Arg Ala Leu Ala Glu Pro Val Thr Ser Thr Pro His Glu
        35                  40                  45

Glu Ser Ala Tyr Gly Pro Leu Gly Val Arg Asp Val Glu Phe Ser Gly
    50                  55                  60

Ala Leu Gly Asp Arg Val Arg Ala Trp His Leu Arg Pro Ala Gly Asp
65                  70                  75                  80

Asp Pro Leu Pro Thr Ala Val Val Phe Ile Gly Tyr Gly Gly Gly Arg
                85                  90                  95

Gly Thr Pro Thr Glu His Ala Trp Leu Ala Ala Ala Gly Tyr Gly Val
            100                 105                 110

Leu Val Val Asp Thr Arg Gly Gln Gly Gly Arg Trp Thr Thr Gly Ala
        115                 120                 125

Thr Ala Asp Ser Ala Pro Ser Gly Pro Ser His Pro Gly Phe Met Thr
    130                 135                 140

Arg Gly Ile Thr Ser Pro Glu Gly Tyr Tyr Tyr Thr Arg Leu Met Thr
145                 150                 155                 160

Asp Ala Ala Leu Ala Val Asp Val Ala Ala Gly Leu Asp Gly Val Asp
                165                 170                 175

Pro Glu Arg Ile Ala Val Leu Gly Ala Ser Gln Gly Gly Gly Leu Ala
            180                 185                 190

Leu Ala Ala Ala Ala Leu Asn Pro Thr Lys Val Lys Val Cys His Ala
        195                 200                 205

Asp Val Pro Phe Leu Cys Asp Phe Gln Arg Ala Ile Thr Leu Thr Gly
```

```
                 210                 215                 220
Ala Asp Pro Tyr Ala Glu Ile Ala Asn Phe Leu Ser His Asn Val Ala
225                 230                 235                 240

Leu Val Lys Gln Val Arg Glu Thr Leu Thr Tyr Val Asp Ala Ala Leu
                245                 250                 255

Leu Ser Arg Arg Ile Thr Ala Thr Ser Leu Leu Ser Ala Gly Leu Met
                260                 265                 270

Asp Glu Val Ser Pro Ser Thr Val Phe Ala Ala Tyr Asn Glu Ile
                275                 280                 285

Thr Ala Pro Lys Arg Ile Glu Val Phe Pro Phe Ser Gly His Ala Val
                290                 295                 300

Pro Arg Thr His Asp Glu Val Lys Leu Lys His Leu Arg Glu His Leu
305                 310                 315                 320

<210> SEQ ID NO 15
<211> LENGTH: 963
<212> TYPE: DNA
<213> ORGANISM: artificial sequence
<220> FEATURE:
<223> OTHER INFORMATION: synthetic construct

<400> SEQUENCE: 15
atgccatggt ttgacctgcc agaagcagag ctcgcgcaat accgcacccc gacgccggag      60
ccagcgggct tggacgcgtg gtgggcggag cgtctggcgg aggcgcgtgc gctggccgaa     120
ccggttacca gcaccccgca cgaagagtcc gcgtatggtc cgctgggcgt ccgtgacgtg     180
gaattttccg cgcactggg cgatcgcgtc cgcgcgtggc acctgcgtcc ggctggcgat     240
gacccgctgc cgacggcggt cgtattcatt ggttacggtg gtggtcgtgg taccccgacc     300
gagcatgcct ggctggccgc agcaggttac ggcgtgctgg ttgtcgatac cgcggtcag     360
ggtggtcgtt ggacgaccgg tgcgacggct gattctgcgc cgagcggtcc gagccatccg     420
ggtttcatga ctcgcggtat tacgagcccg gagggctatt actatacccg tctgatgacc     480
gatgctgcac tggcggtgga cgttgcagcc ggcctggatg gcgtggatcc ggaacgtatc     540
gccgtgctgg tgcatcgca aggcggtggc ctggcgttgg cagccgcagc tctgaacccg     600
accaaagtta aggtctgcca cgccgatgtt ccgtttctgt gcgacttcca gcgtgccatt     660
acgctgacgg gtgcggaccc gtacgcggag atcgcgaatt tcttgtctca taatgtcgcc     720
ctggtgaagc aggttcgtga aaccctgact tacgtggacg cggctctgct gagccgtcgt     780
atcaccgcaa ctagcctgtt gagcgcaggt ctgatggacg aagttacccc tccgagcacc     840
gtgtttgcgg cgtataacga gatcacggct cctaaacgta ttgaggtttt cccgtttagc     900
ggccacgcgg ttccgcgcac ccacgacgaa gtcaaattga agcatctgcg cgagcacctg     960
taa                                                                   963

<210> SEQ ID NO 16
<211> LENGTH: 320
<212> TYPE: PRT
<213> ORGANISM: artificial sequence
<220> FEATURE:
<223> OTHER INFORMATION: synthetic construct

<400> SEQUENCE: 16

Met Pro Trp Phe Asp Leu Pro Glu Ala Glu Leu Ala Gln Tyr Arg Thr
1               5                   10                  15

Pro Thr Pro Glu Pro Ala Gly Leu Asp Ala Trp Ala Glu Arg Leu
                20                  25                  30
```

```
Ala Glu Ala Arg Ala Leu Ala Glu Pro Val Thr Ser Thr Pro His Glu
            35                  40                  45

Glu Ser Ala Tyr Gly Pro Leu Gly Val Arg Asp Val Glu Phe Ser Gly
        50                  55                  60

Ala Leu Gly Asp Arg Val Arg Ala Trp His Leu Arg Pro Ala Gly Asp
65                  70                  75                  80

Asp Pro Leu Pro Thr Ala Val Val Phe Ile Gly Tyr Gly Gly Gly Arg
                85                  90                  95

Gly Thr Pro Thr Glu His Ala Trp Leu Ala Ala Gly Tyr Gly Val
            100                 105                 110

Leu Val Val Asp Thr Arg Gly Gln Gly Arg Trp Thr Thr Gly Ala
            115                 120                 125

Thr Ala Asp Ser Ala Pro Ser Gly Pro Ser His Pro Gly Phe Met Thr
        130                 135                 140

Arg Gly Ile Thr Ser Pro Glu Gly Tyr Tyr Tyr Thr Arg Leu Met Thr
145                 150                 155                 160

Asp Ala Ala Leu Ala Val Asp Val Ala Ala Gly Leu Asp Gly Val Asp
                165                 170                 175

Pro Glu Arg Ile Ala Val Leu Gly Ala Ser Gln Gly Gly Gly Leu Ala
            180                 185                 190

Leu Ala Ala Ala Ala Leu Asn Pro Thr Lys Val Lys Val Cys His Ala
            195                 200                 205

Asp Val Pro Phe Leu Cys Asp Phe Gln Arg Ala Ile Thr Leu Thr Gly
        210                 215                 220

Ala Asp Pro Tyr Ala Glu Ile Ala Asn Phe Leu Ser His Asn Val Ala
225                 230                 235                 240

Leu Val Lys Gln Val Arg Glu Thr Leu Thr Tyr Val Asp Ala Ala Leu
                245                 250                 255

Leu Ser Arg Arg Ile Thr Ala Thr Ser Leu Leu Ser Ala Gly Leu Met
            260                 265                 270

Asp Glu Val Thr Pro Pro Ser Thr Val Phe Ala Ala Tyr Asn Glu Ile
        275                 280                 285

Thr Ala Pro Lys Arg Ile Glu Val Phe Pro Phe Ser Gly His Ala Val
        290                 295                 300

Pro Arg Thr His Asp Glu Val Lys Leu Lys His Leu Arg Glu His Leu
305                 310                 315                 320

<210> SEQ ID NO 17
<211> LENGTH: 325
<212> TYPE: PRT
<213> ORGANISM: artificial sequence
<220> FEATURE:
<223> OTHER INFORMATION: synthetic construct

<400> SEQUENCE: 17

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80
```

```
Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 18
<211> LENGTH: 325
<212> TYPE: PRT
<213> ORGANISM: artificial sequence
<220> FEATURE:
<223> OTHER INFORMATION: synthetic construct

<400> SEQUENCE: 18

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110
```

```
Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
                180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
                325
```